(12) United States Patent  
Kuzma

(10) Patent No.: US 6,397,110 B1
(45) Date of Patent: May 28, 2002

(54) COCHLEAR ELECTRODE SYSTEM INCLUDING DETACHABLE FLEXIBLE POSITIONER

(75) Inventor: Janusz A. Kuzma, Englewood, CO (US)

(73) Assignee: Advanced Bionics Corporation, Sylmar, CA (US)

(*) Notice: Subject to any disclaimer, the term of this patent is extended or adjusted under 35 U.S.C. 154(b) by 0 days.

(21) Appl. No.: 09/443,627

(22) Filed: Nov. 19, 1999

Related U.S. Application Data

(63) Continuation-in-part of application No. 09/140,034, filed on Aug. 26, 1998, now Pat. No. 6,038,484.

(51) Int. Cl.⁷ ................................................. A61N 1/05
(52) U.S. Cl. ..................................................... 607/137
(58) Field of Search .......................................... 607/137

(56) References Cited

U.S. PATENT DOCUMENTS

| | | | |
|---|---|---|---|
| 4,819,647 A | 4/1989 | Byers et al. ............... | 128/642 |
| 5,545,219 A | 8/1996 | Kuzma ....................... | 623/10 |
| 5,645,585 A | 7/1997 | Kuzma ....................... | 623/10 |
| 5,833,714 A | 11/1998 | Loeb .......................... | 607/56 |
| 5,999,859 A | * 12/1999 | Jolly ......................... | 607/137 |

* cited by examiner

Primary Examiner—Carl Layno
(74) Attorney, Agent, or Firm—Bryant R. Gold

(57) ABSTRACT

An electrode system includes (1) an electrode array, made in a straight or curved shape, but made on a flexible carrier so that it can easily bend within a curved body cavity, such as the cochlea; and (2) a flexible positioner, molded in a curved or straight shape from a silicone polymer so as to make it easy to slide into the body cavity. Some embodiments may further include an electrode and/or a positioner guiding insert. One embodiment of the positioner includes keeper tabs at its distal end, and side walls at its proximal end, to help maintain the positioner in a desired position along the back side of the electrode array during and after the insertion process. Engagement members at a distal end of the positioner also allow detachable engagement with corresponding or mating members near the distal end of the electrode array during the insertion process, thereby allowing insertion of the positioner to cause engagement of the positioner with the electrode array, and to provide for deeper insertion of the electrode array as the positioner is inserted deeper into the cochlea. One method of insertion involves first inserting an electrode array into the scala tympani, and then second inserting the positioner into the scala tympani so as to lie between the electrode array and the outer wall of the scala tympani, thereby forcing the electrode array against the modiolar wall.

52 Claims, 22 Drawing Sheets

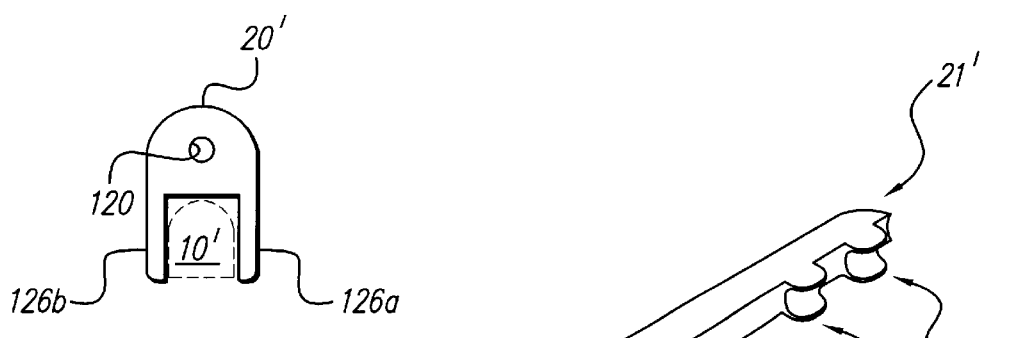
FIG. 8A
FIG. 8B
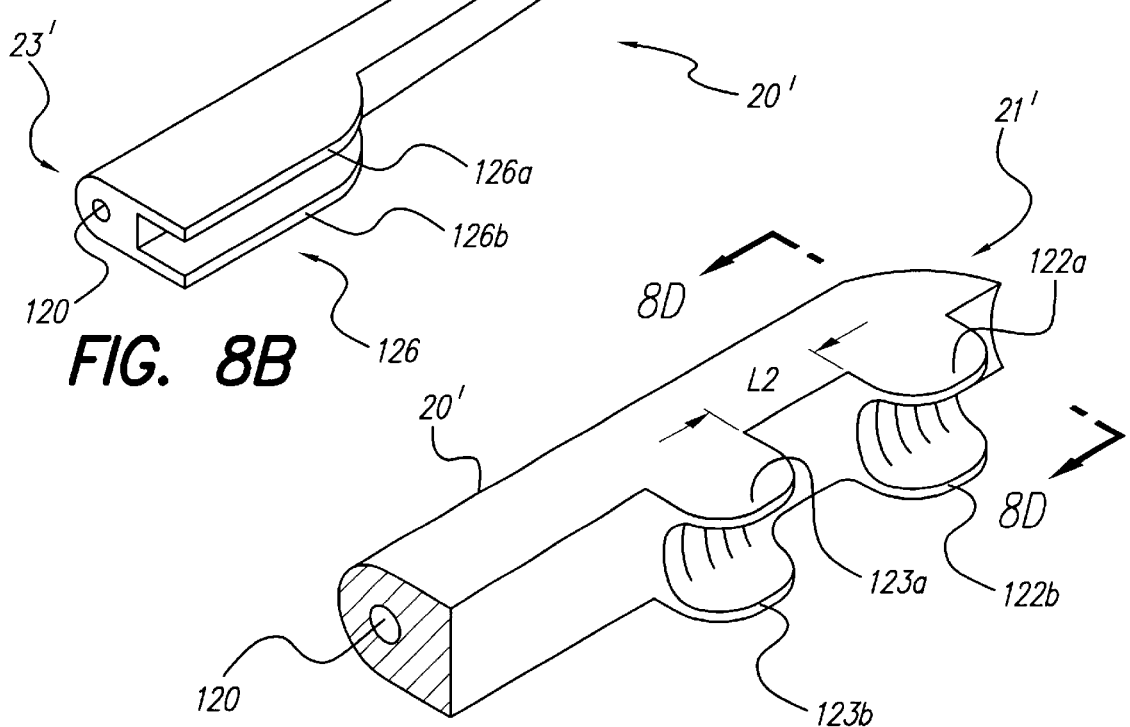
FIG. 8C
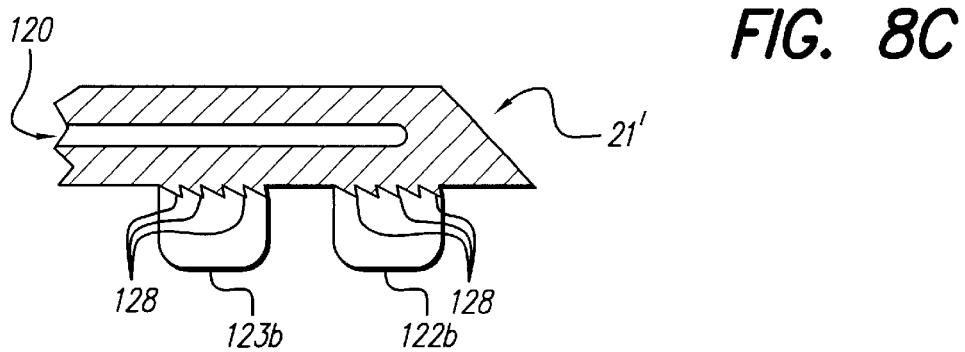
FIG. 8D

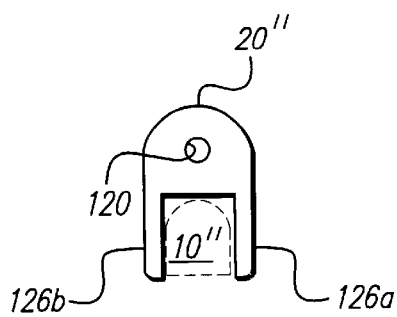
FIG. 8E
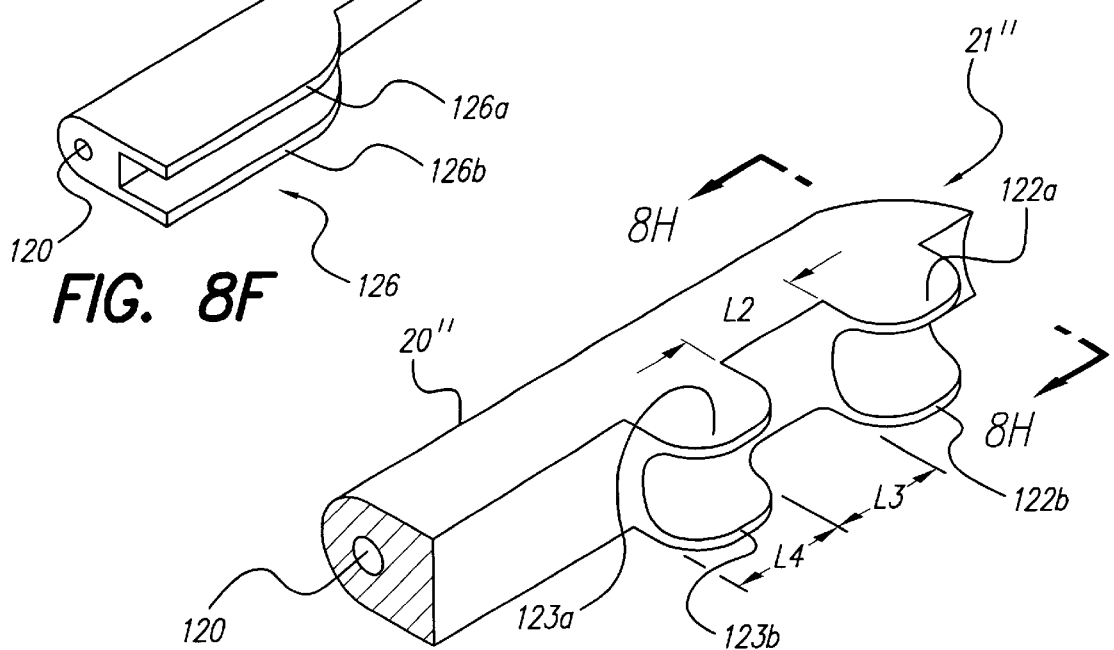
FIG. 8F
FIG. 8G
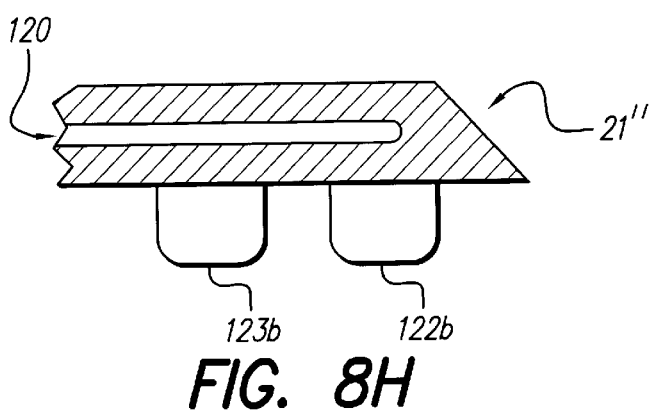
FIG. 8H

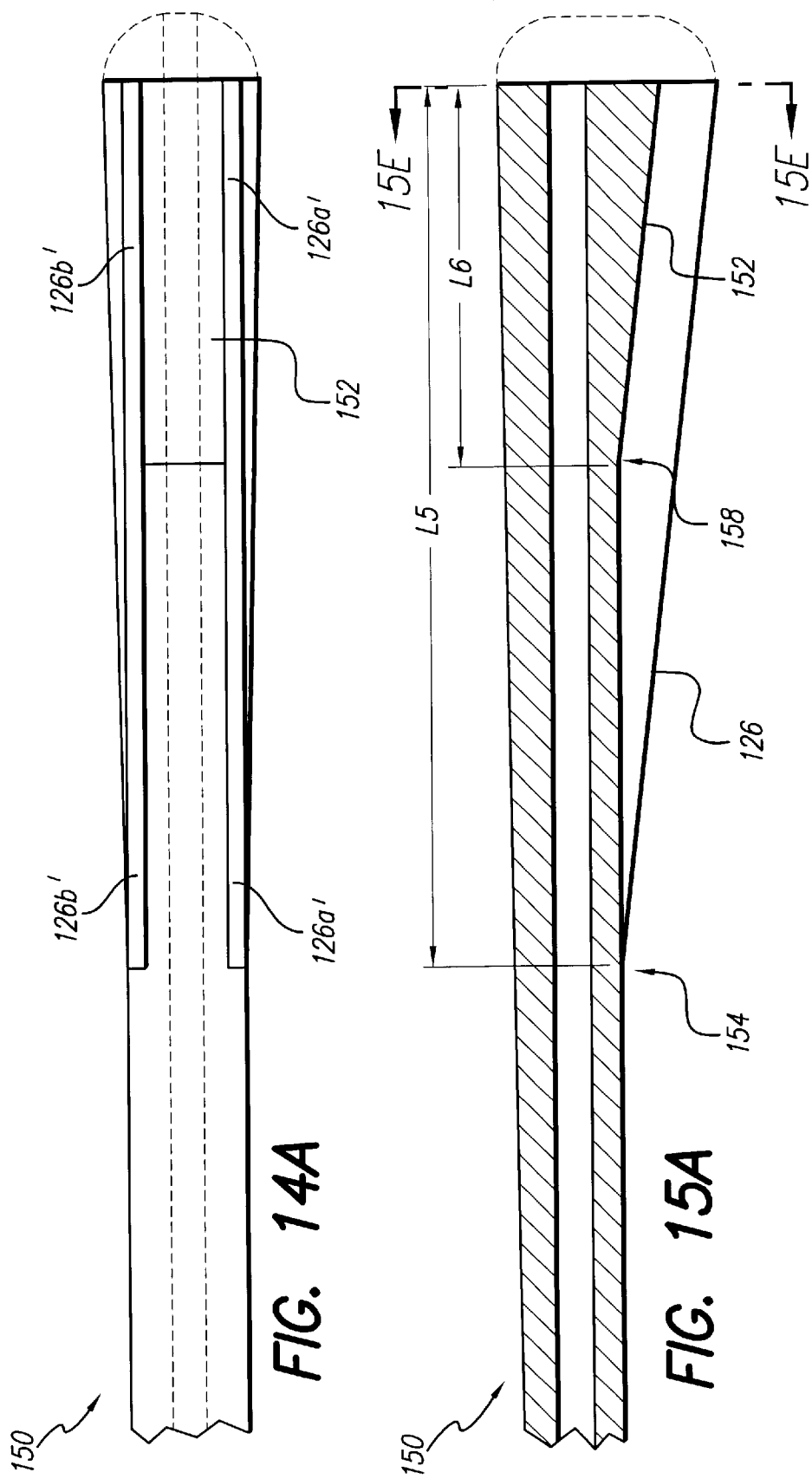

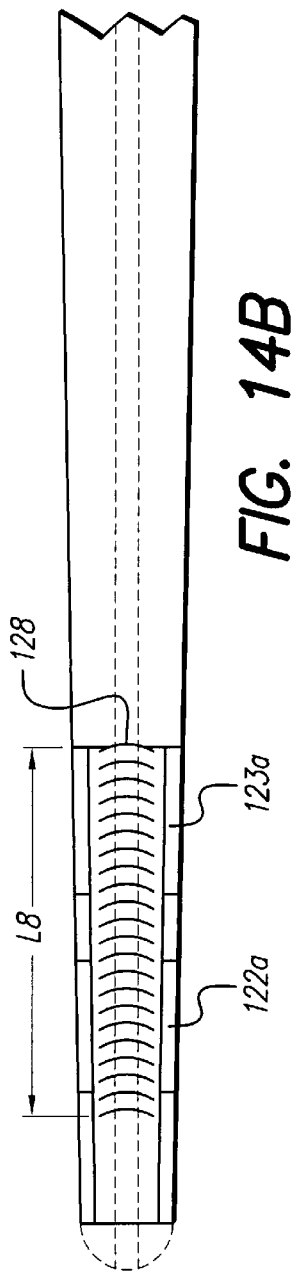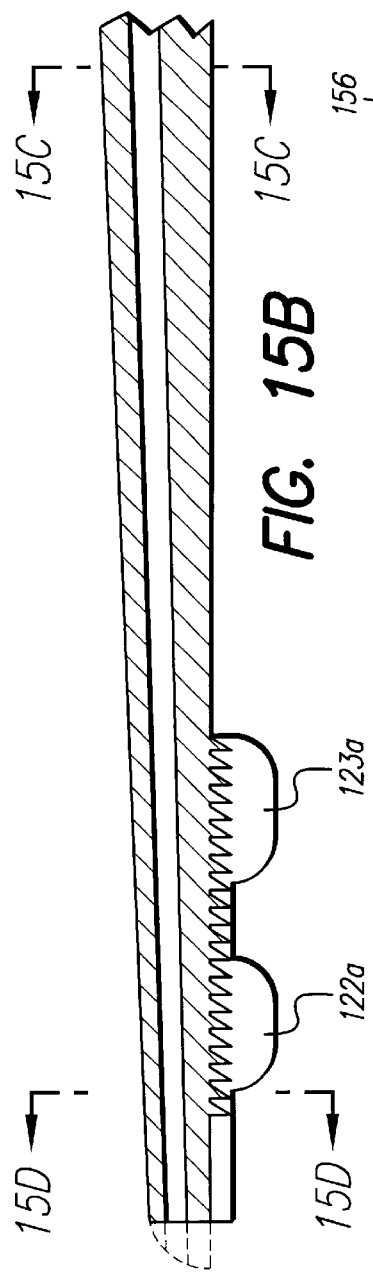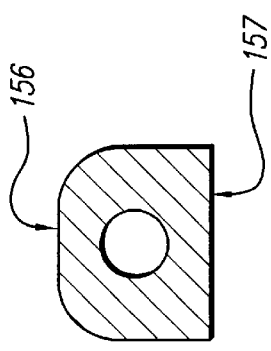

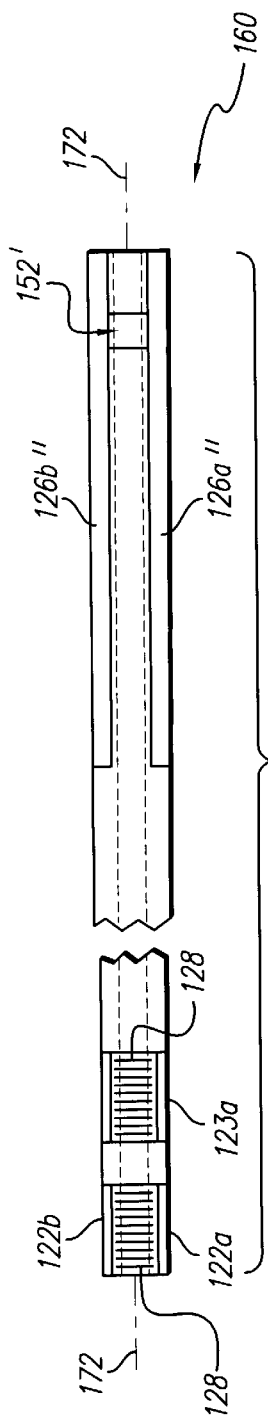
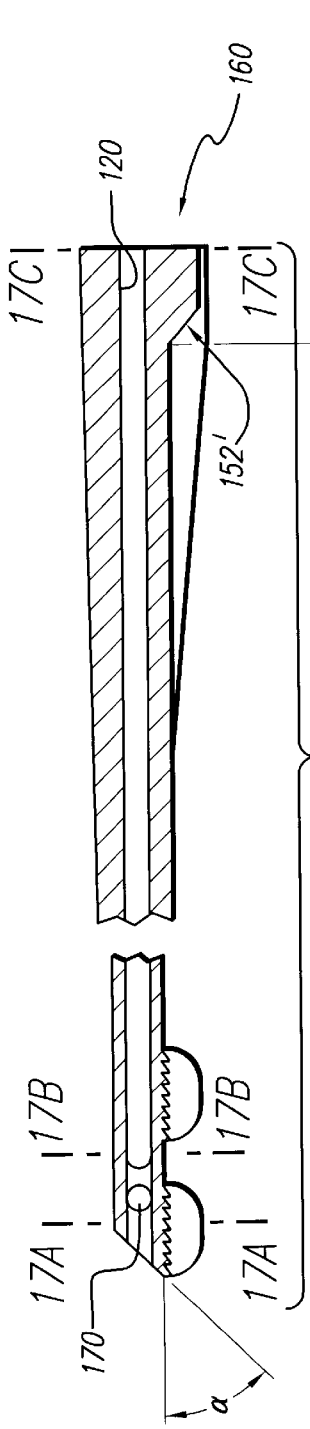
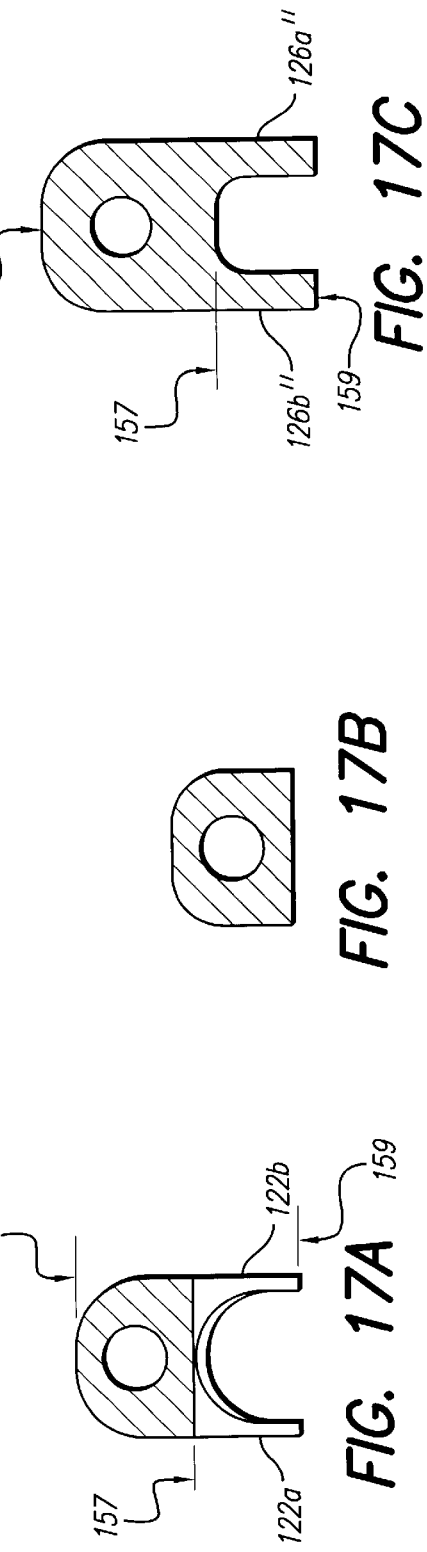

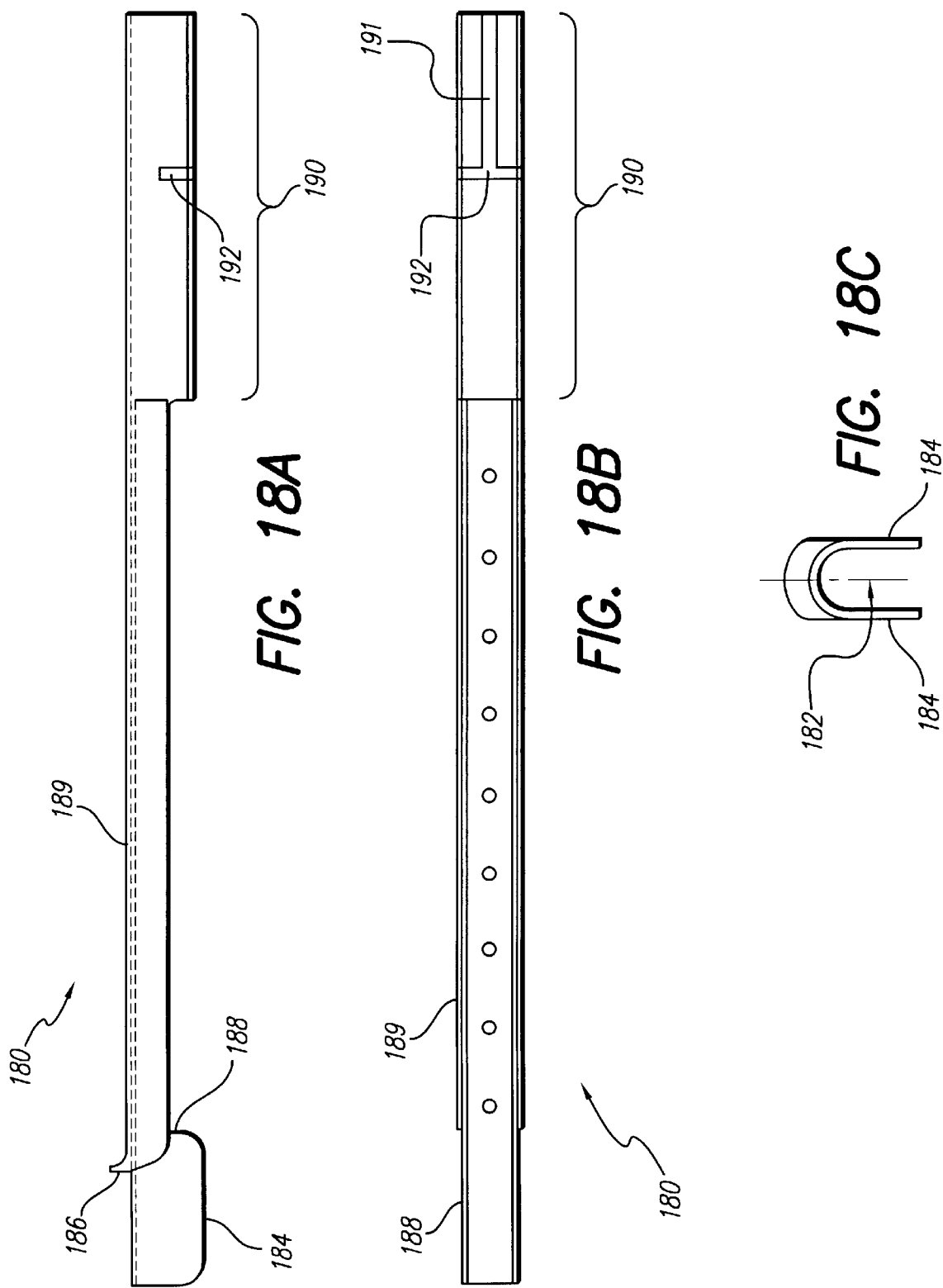

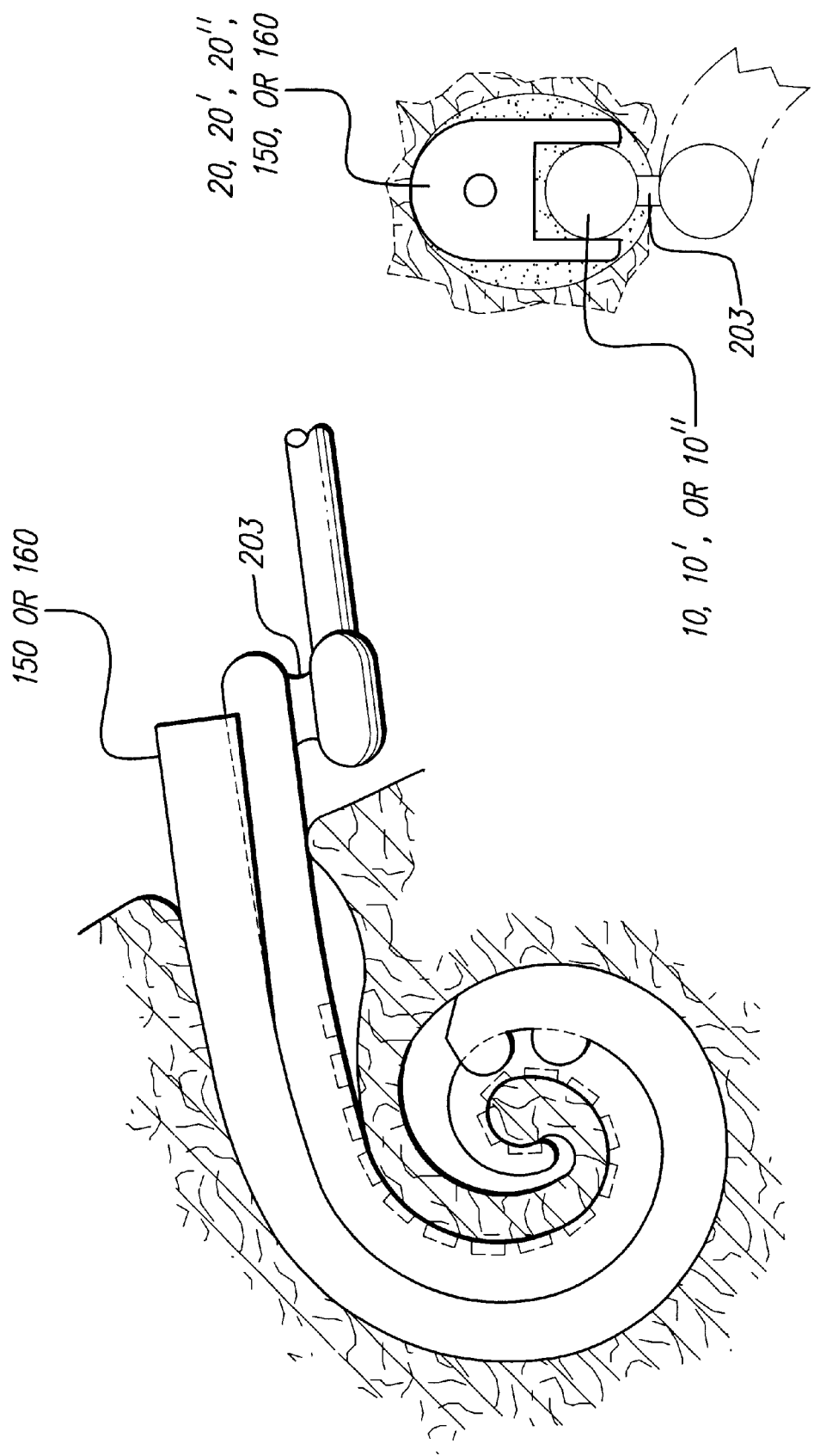

COCHLEAR ELECTRODE SYSTEM INCLUDING DETACHABLE FLEXIBLE POSITIONER

This application is a continuation-in-part (CIP) of U.S. patent application Ser. No. 09/140,034, filed Aug. 26, 1998 now U.S. Pat. No. 6,038,484, which patent application is incorporated herein by reference.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types, of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it has long been known that an enhanced performance of a cochlear implant can be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing an electrode system that allows for correct positioning of the electrode contacts against the modiolar wall of the cochlea. Such "correct" positioning is achieved through the use of an electrode system that includes the following three main components: (1) an electrode array, made in a straight or slightly curved shape, made on a flexible carrier so that it can easily bend within the cochlea; (2) a flexible positioner, typically molded from a silicone polymer so as to make it easy to slide into the cochlea, and made to assume a curved shape to facilitate its insertion into the cochlea; and (3) a guiding insert or guide tube, made from a biocompatible material, such as platinum (Pt), titanium (Ti) or Teflon, for facilitating the insertion of either the electrode array or the flexible positioner.

In one embodiment, insertion of the electrode array is performed in three main steps. First, the flexible positioner is inserted through the appropriate dimension of cochleostomy. This means it is inserted into the scala tympani (one of the channels of the cochlea) to the desired depth. The desired depth typically involves a rotation of about 360 degrees and causes the positioner to rest against the outer or lateral wall of the scala tympani, leaving an opening slightly larger than the cross-section of the electrode array adjacent the inner wall of the scala tympani. Advantageously, the super-flexible nature of the positioner prevents it from causing damage to the cochlear structure. At the same time, once inserted, it provides a guide for the electrode, and protects the cochlear walls from being damaged or touched directly by the stiffer electrode body.

Second, after insertion of the positioner to the desired depth, the guiding insert may be pushed into the opening of the cochlear.

Third, the electrode array is inserted through the opening of the guiding insert to the desired depth. This desired depth is preferably beyond the depth of the positioner. The distal end of the array advantageously includes one or more engaging or locking barbs or teeth that engage with corresponding barbs or teeth at the distal end of the positioner. At this stage, the electrode is positioned very close to the modiolus of the cochlea. Then, as a final optimization of the position of the electrode contacts of the electrode array, the electrode array is pulled back slightly (about 2 mm). This backward motion assures that the distal tips of the electrode array and the positioner are engaged by the barbs located thereon. Such engagement may further serve to force the electrodes into direct contact with the modiolar wall.

In another embodiment, a similar procedure is followed, except that the electrode array is inserted into the cochlea first, and then the positioner is inserted through the guide tube so as to lie along a back side (i.e., the side opposite the electrode contacts) of the electrode array, thereby positioning the electrode contacts of the array near the modiolar wall. In such embodiment, the positioner advantageously has at least one pair of guide tabs, or wings, at or near its distal tip, so as to keep the distal tip of the positioner from slipping off of the distal tip of the electrode array. In other words, the tabs or wings at the distal tip of the positioner, form a channel, or groove, through which the body of the electrode array may slide as the positioner is inserted behind the electrode array, and which once inserted, keep the positioner distal tip in a desired position alongside (and, more particularly, along a back side of) the distal tip of the electrode array. In such embodiment, the positioner also may include a pair of flexible side walls near or at its proximal end. The space between such side walls also forms a channel or groove into which the body of the electrode array may be positioned as the positioner is slid into position alongside the electrode array within the cochlea. Such channel or groove may further include a sloping floor that acts as an additional spacer that pushes or forces a proximal end of the electrode array into close engagement with the basal end of the cochlea as the positioner is fully inserted into the cochlea.

In accordance with an alternate embodiment of the invention, an electrode positioner is provided that may be used with almost any electrode array that is to be inserted into the cochlea in order to assure that a desired modiolar-hugging position is achieved with the electrode contacts of the array.

In accordance with yet an additional embodiment of the invention, a cochlear electrode system is provided that includes (1) an electrode array and (2) an electrode positioner. Using a preferred insertion technique or method, the electrode array is first inserted into the cochlea as far as it reasonably can be; then the positioner is inserted into the cochlea, behind the electrode array so as to force or push the electrode contacts of the array against the modiolar wall. As required, a guide tube may be used to assist with inserting the electrode positioner into the cochlea. Moreover, as the positioner is thus inserted into the cochlea behind the electrode array, the positioner carries the electrode deeper into the cochlea, e.g., approximately ½ turn deeper. In such instance, the positioner need not be equipped with internal barbs at its distal end, but it may be.

Advantageously, the electrode system of the present invention achieves the following goals: (1) it helps assure that the electrode array is optimally positioned against the modiolar wall in a cochlea of any size; (2) the insertion of the electrode array avoids or produces minimal trauma to the cochlear structure; (3) it allows deep insertion beyond 360 degrees; (4) it can be manufactured using easy, low cost technology; and (5) the electrode and/or the positioner can be easily removed and reinserted, if required.

BRIEF DESCRIPTION OF THE DRAWINGS

The above and other features and advantages of the present invention will be more apparent from the following more particular description thereof, presented in conjunction with the following drawings wherein:

FIGS. 8A, 8B, 8C and 8D illustrate an alternative embodiment of a positioner best suited for use with the electrode array embodiment shown in FIGS. 7A and 7B, with FIG. 8A showing a view of the positioner from its proximal end, FIG. 8B showing a perspective view of the positioner, FIG. 8C showing an enlarged perspective view of the distal tip region of the positioner, and FIG. 8D showing a sectional view of the distal tip region of the positioner;

FIGS. 8E, 8F, 8G and 8H illustrate yet an additional embodiment of a positioner best suited for use with the electrode array embodiment shown in FIGS. 7C and 7D, with FIG. 8E showing a view of the positioner from its proximal end, FIG. 8F showing a perspective view of the positioner, FIG. 8G showing an enlarged perspective view of the distal tip region of the positioner, and FIG. 8H showing a sectional view of the distal tip region of the positioner;

FIG. 14A is a bottom view of the proximal end of the positioner of FIG. 13, looking at the side of the positioner that lies adjacent the electrode array when the positioner is inserted alongside the electrode array within the cochlea;

FIG. 14B is a bottom view of the distal end of the positioner of FIG. 13, looking at the side of the positioner that lies adjacent the electrode array when the positioner is inserted alongside the electrode array within the cochlea;

FIG. 15A is a section view, rotated 90° from the view shown in FIG. 14A, of the proximal end of the positioner of FIG. 13;

FIG. 15B is a section view, rotated 90° from the view shown in FIG. 14B, of the distal end of the positioner of FIG. 13;

FIG. 15C is a sectional view of the positioner of FIG. 15B taken near the middle of the positioner along the line 15C—15C;

FIG. 15D is a sectional view of the positioner of FIG. 15B taken near the distal tip along the line 15D—15D;

FIG. 16 is a bottom segmented view of another variation of a positioner that may be used with the present invention, looking at the side of the positioner that lies adjacent the electrode array when the positioner is inserted alongside the electrode array within the cochlea;

FIG. 17 is a side segmented section view, rotated 90° from the view shown in FIG. 16, of the positioner;

FIGS. 17A, 17B and 17C are sectional views, taken along the lines 17A—17A, 17B—17B, and 17C—17C of FIG. 17, respectively;

FIG. 18A is a side view of an insertion tube that may be used to guide the positioner of the present invention as it is inserted into the cochlea along a back side of a previously-inserted electrode array;

FIG. 18B is a bottom view of the insertion tube of FIG. 18A;

FIG. 18C is a distal end view of the insertion tube of FIG. 18A;

FIGS. 19A, 19B, 19C and 19D respectively illustrate the four main steps utilized to insert an electrode array into the cochlea using the electrode system of the present invention; and FIG. 19E depicts a proximal end view of the electrode system after the electrode array and positioner have been inserted into the cochlea using the method depicted in FIGS. 19A–19D.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches one type of electrode system that may be used with a cochlear stimulation system. Other electrodes and electrode systems may also be used for this purpose as disclosed, e.g., in Applicant's previously-filed patent applications Ser. No. 09/140,033, filed Aug. 26, 1998, now U.S. Pat. No. 6,070,105; Ser. No. 09/140,035, filed Aug. 26, 1998, now U.S. Pat. No. 6,125,302; Ser. No. 09/247,734, filed Feb. 9, 1999, now U.S. Pat. No. 6,129,753; and Ser. No. 09/298,410, filed Apr. 23, 1999, now U.S. Pat. No. 6,195,586; all of which are incorporated herein by reference. The materials, dimensions, methods of manufacture, and the like, described in these referenced applications/patents are also applicable to the present invention.

Figure 1A:
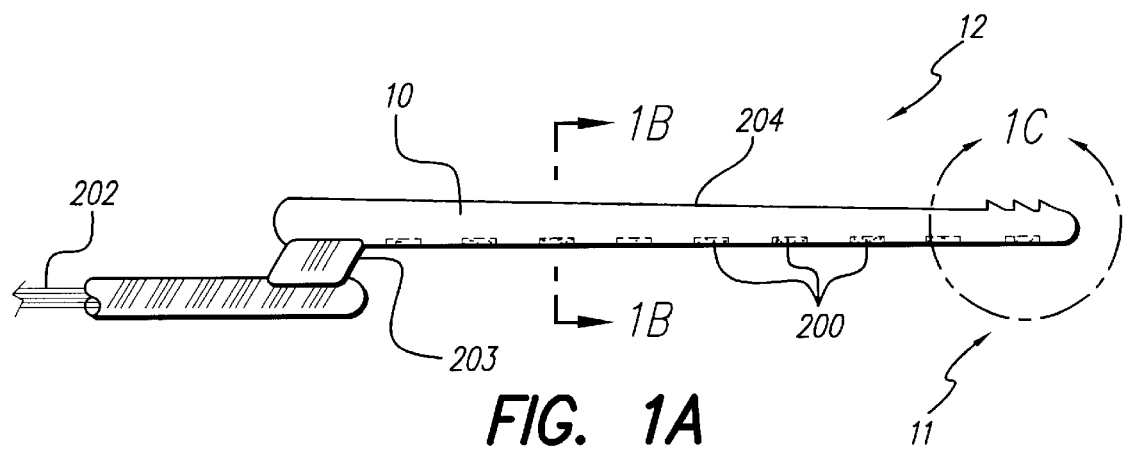
FIGS. 1A and 1B show a side and cross-sectional view, respectively, of one embodiment of an electrode array which may form part of the electrode system of the present invention.
Figure 1B:
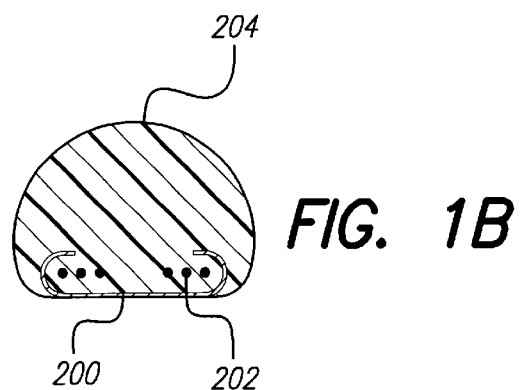

Turning first to FIGS. 1A and 1B, there is shown a side and a cross-sectional view, respectively, of an electrode array 10 that forms part of an electrode system 12 made in accordance with one embodiment of the present invention. The cross-sectional view of FIG. 1B is taken along the line 1B—1B of FIG. 1A. A distal end portion 11 of the array 10 is shown in FIG. 1C.

Figure 1C:
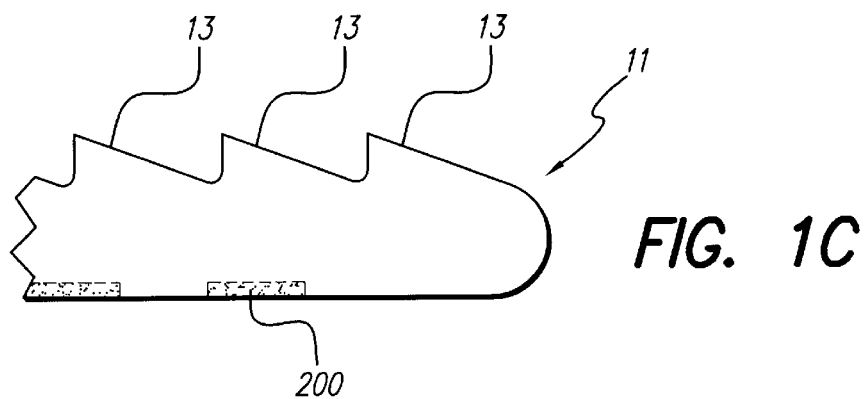
FIG. 1C illustrates an enlarged view of the engaging barbs used at a distal end of the electrode array shown in FIG. 1A.

As seen in FIGS. 1A, 1B and 1C, the electrode array 10 includes a plurality of spaced-apart electrode contacts 200, formed within or carried on a flexible carrier 204. Each of the electrodes is connected to at least one wire 202 which is embedded within the carrier 204. A proximal end of the these wires 202 (not shown) allows selective electrical connection to be made with each electrode contact 200 through use of a tissue stimulator, e.g., a cochlear stimulator. An offset portion 203, or bend, is formed in the carrier 204 to facilitate insertion of the electrode array 10 into the cochlea. Such offset 203, inter alia, not only identifies the side of the carrier 204 on which the electrodes 200 are located, but also serves as a physical stop that prevents insertion of the electrode array 10 into the scala tympani 102 of the cochlea 100 to a depth deeper than is desired. (Note, hereafter, the "electrode contacts 200" carried on the electrode array 10 may be referred to simply as the "electrodes 200".)

As an important feature of the invention, in some embodiments, the distal end portion 11 of the electrode array 10 includes a plurality of engaging members, e.g., sloping barbs or teeth 13. These barbs 13, as explained below, help maintain the electrode array 10 in its desired position against the modiolus wall of the cochlea once it is inserted into the cochlea.

Figure 2A:
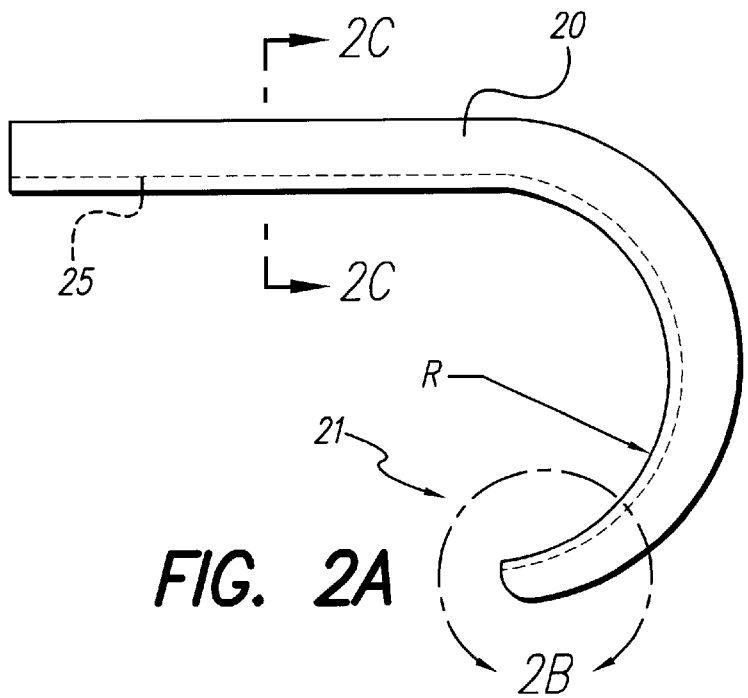
FIGS. 2A and 2C show a side and cross-sectional view, respectively, of a curved positioner that may also form part of the electrode system of the present invention.
Figure 2B:
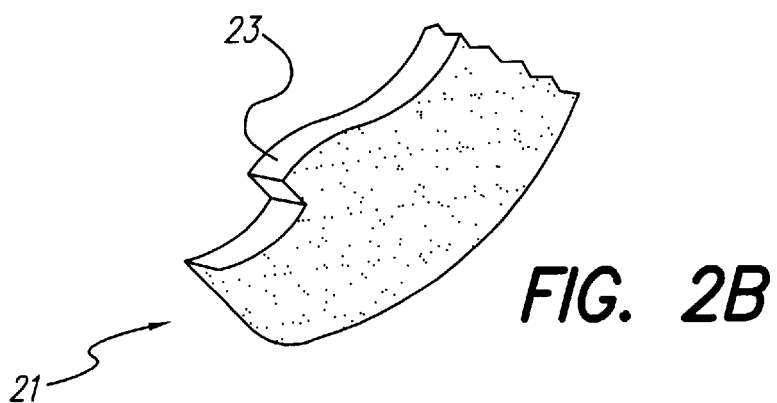
FIG. 2B depicts an enlarged view of a distal end of the positioner shown in FIG. 2A.
Figure 2C:
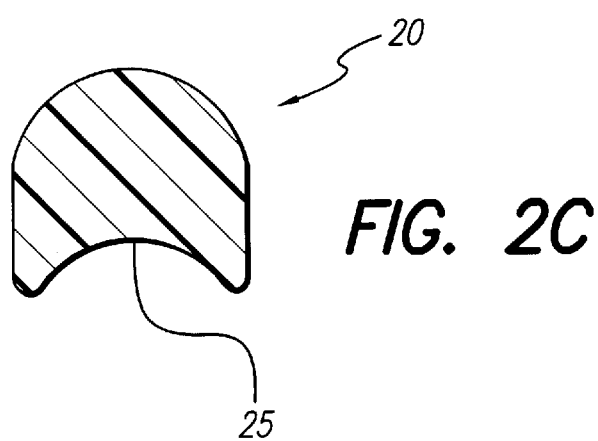

A second component of the electrode system of the present invention is a positioner 20, as illustrated in FIGS. 2A, 2B and 2C. FIG. 2A shows a side view of the positioner 20. FIG. 2B shows an enlarged view of a distal end portion 21 of the positioner 20, including a barb 23 or other suitable engaging member. Typically, the distal end of the positioner 20 will include a plurality of barbs 23, other engaging members, formed therein. FIG. 2C shows a cross-sectional view of the positioner 20 taken along the line 2C—2C of FIG. 2A. As seen in FIG. 2C, the positioner 20 typically includes a shallow smooth groove or channel 25 located along one side thereof. This channel or groove 25, as seen by the dotted-line representation of the bottom of the channel in FIG. 2A, traverses the entire length of the positioner 20. Such channel or groove 25 is not necessary for all embodiments of the positioner 20.

The flexible positioner 20 is preferably made from a silicone polymer, and may be molded to assume the curved shape shown in FIG. 2A, or it may be molded to assume a more straightened shape. If curved, the radius of curvature "R" is selected to be somewhat larger than the natural curvature of the cochlea. That is, when inserted into the cochlea, the positioner 20 will ideally have a tighter wind or coil than that afforded by its formed curved shape. This assures that when inserted into the cochlea, the positioner 20 is held away from the modiolar wall 104, leaving a cavity or channel 22 (see FIG. 4B) against the modiolar wall. Such channel 22 provides a space wherein the electrode array 10 may be inserted.

Figure 3A:
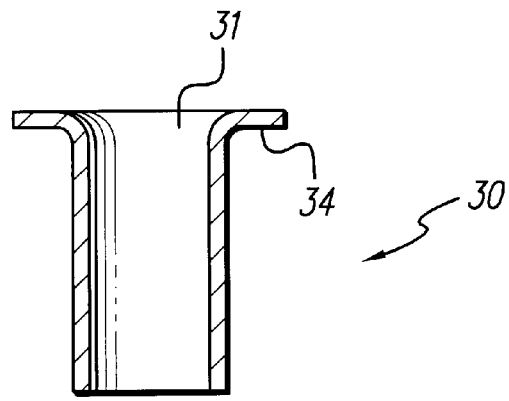
FIGS. 3A, 3B and 3C illustrate a cross-sectional, top, and perspective view, respectively, of an insert that forms part of the electrode system of the present invention, which insert is used to guide the electrode as it is inserted into the cochlea.
Figure 3B:
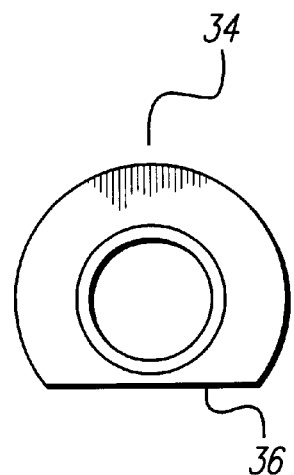
Figure 3C:
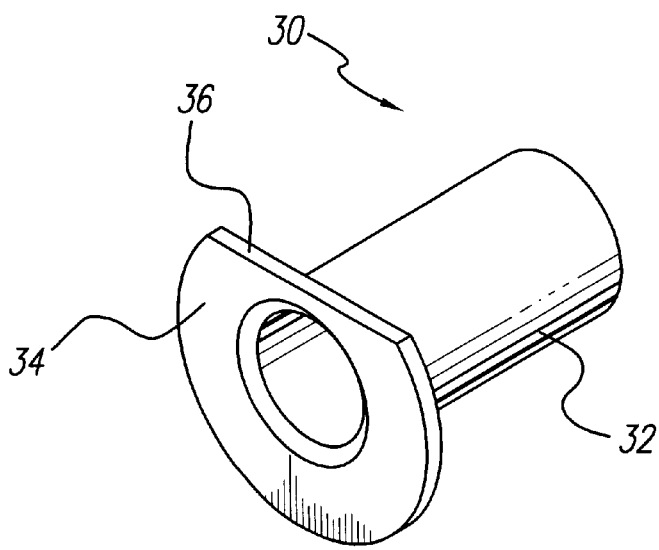
Figure 5:
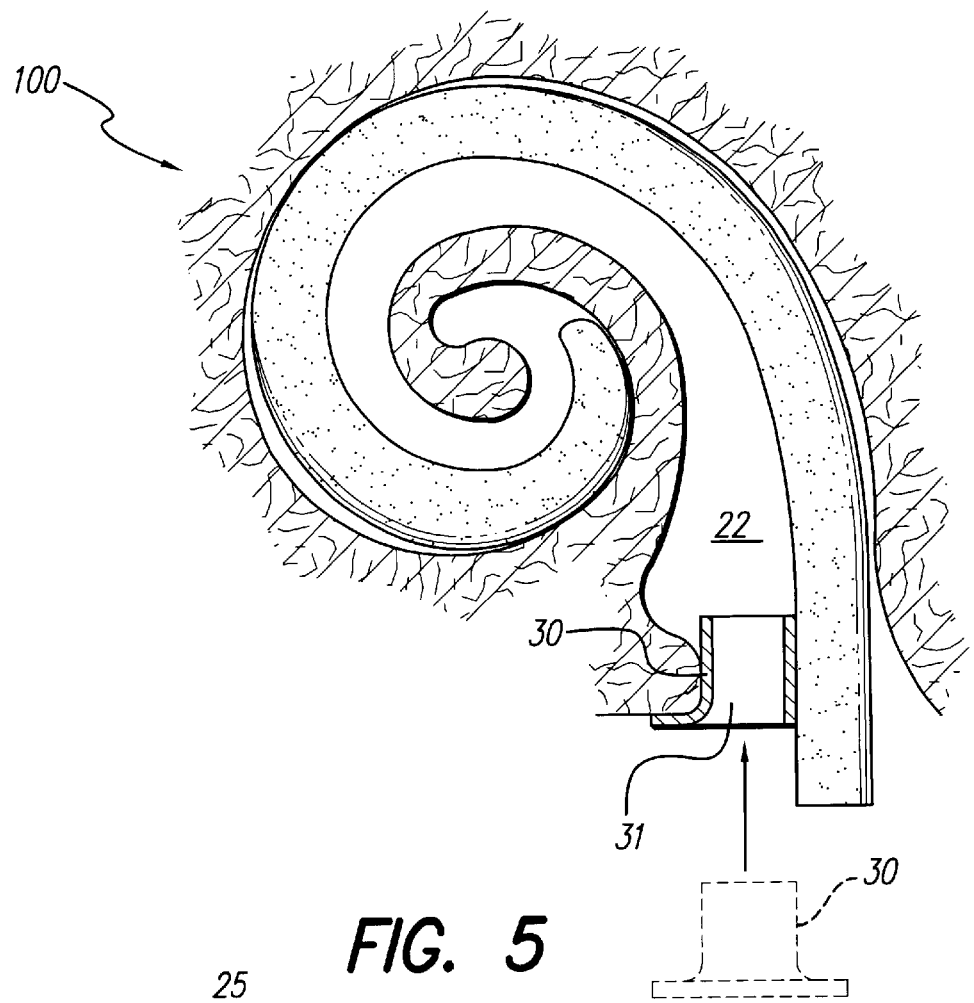
FIG. 5 shows a schematic representation of the spiraling scala tympani of the cochlea with the positioner inserted therein, and further illustrates the placement of an electrode-guiding insert into the front opening of the scala tympani.

A third component of the electrode system, in accordance with at least one embodiment thereof, is an electrode-guide 30 as shown in FIGS. 3A, 3B and 3C. The guide 30 is designed to be inserted into the proximal end of the cavity or channel 22 formed between the modiolus wall and the positioner 20. The guide 30 includes a sleeve portion 32 and a flange portion 34. The sleeve portion 32 includes an opening or channel 31 therein having a size that allows the electrode array 10 (FIG. 1A, 1B) to readily slide therethrough. A portion of the flange 34, as seen best in FIG. 3B, is removed, thereby forming a straight edge 36 on one side of the flange. As will be evident from FIG. 5, below, this removed portion of the flange allows the insert 30 to fit snugly against the positioner 20 (i.e., the straight edge 36 fits up against the positioner 20) when the insert 30 is inserted into the cochlea.

The electrode-guiding insert 30 is made from a biocompatible material, such as platinum (Pt), titanium (Ti) or Teflon.

For some embodiments of the invention, as described more fully below, the electrode-guiding insert 30 is optional, and may be omitted. In still other embodiments of the invention, as is also described more fully below, a guiding insert of the type shown in FIG. 3C, or similar guiding insert, may be used to help insert the positioner 20 into the cochlea after the electrode array 10 has first been inserted therein.

Figure 4A:
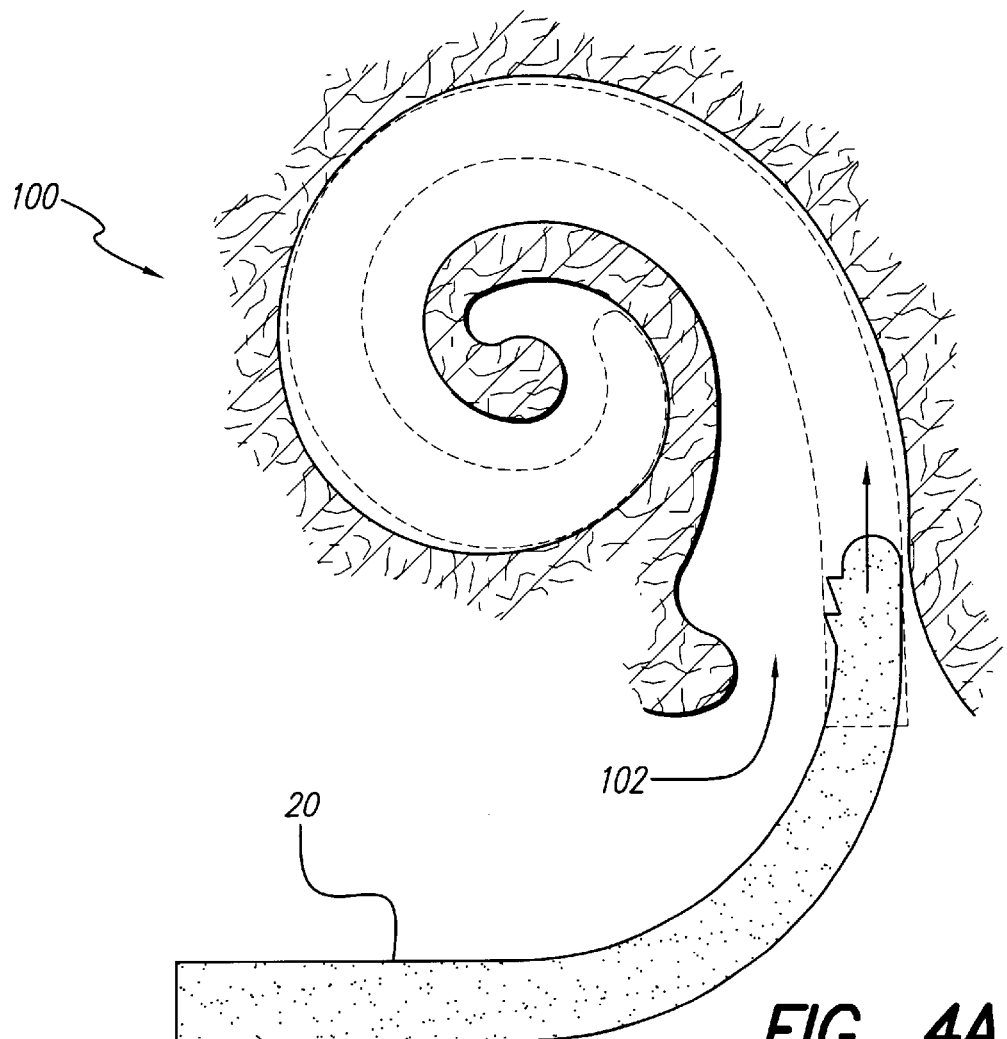
FIG. 4A illustrates insertion of the curved positioner into the scala tympani of the cochlea.
Figure 4B:
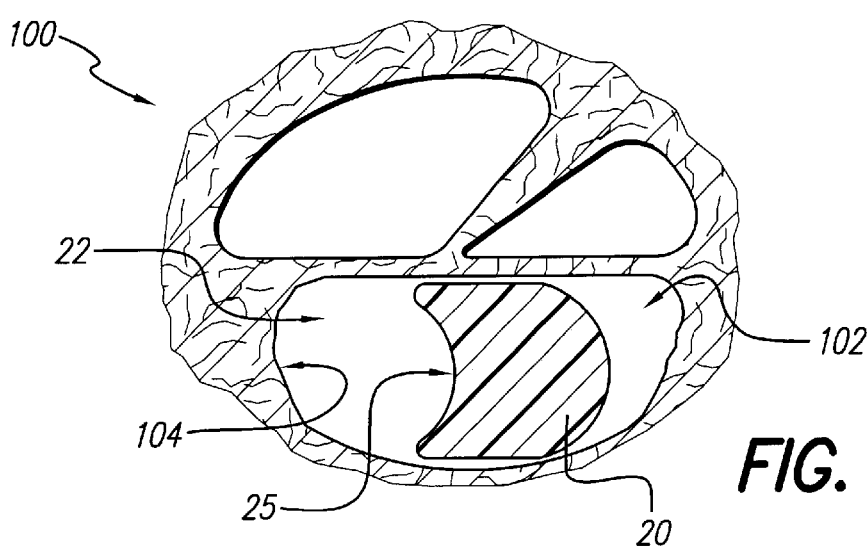
FIG. 4B shows a cross-sectional view of the cochlea with the positioner placed within the scala tympani.

Next, the method of using the electrode system of the present invention will be described in connection with FIGS. 4A through 6B. First, as shown in FIGS. 4A and 4B, the flexible positioner 20 is inserted into the scala tympani 102

(one of the channels of the cochlea 100) to the desired depth. The desired depth typically involves a rotation of about 360 degrees and causes, as seen best in FIG. 4B, the positioner 20 to rest against the outer or lateral wall of the scala tympani 102. This position leaves a channel or opening 22, one side of which is defined by the positioner 20, e.g., the groove 25 of the positioner 20, adjacent the inner wall (modiolus 104) of the scala tympani. The opening 22 is preferably slightly larger than the cross-section of the electrode array 10.

Advantageously, the super-flexible nature of the positioner 20 prevents it from causing damage to the cochlear structure. At the same time, once inserted, the positioner 20 provides a guide for the electrode array 10, and protects the cochlear walls from being damaged or touched directly by the stiffer electrode body 204.

Once the positioner has been inserted to the desired depth, an electrode-guiding insert 30 (if used) is pushed into the opening of the channel 22. When this insertion is performed, the flat or straight side 36 of the flange 30 is placed against the grooved, or inner, side of the positioner 20, as seen best in FIG. 5. (The "inner" side of the positioner, regardless of whether the positioner has a groove or not, is that side on the inside of the curve of the positioner, i.e., that side facing the modiolar wall 104.)

Figure 6A:
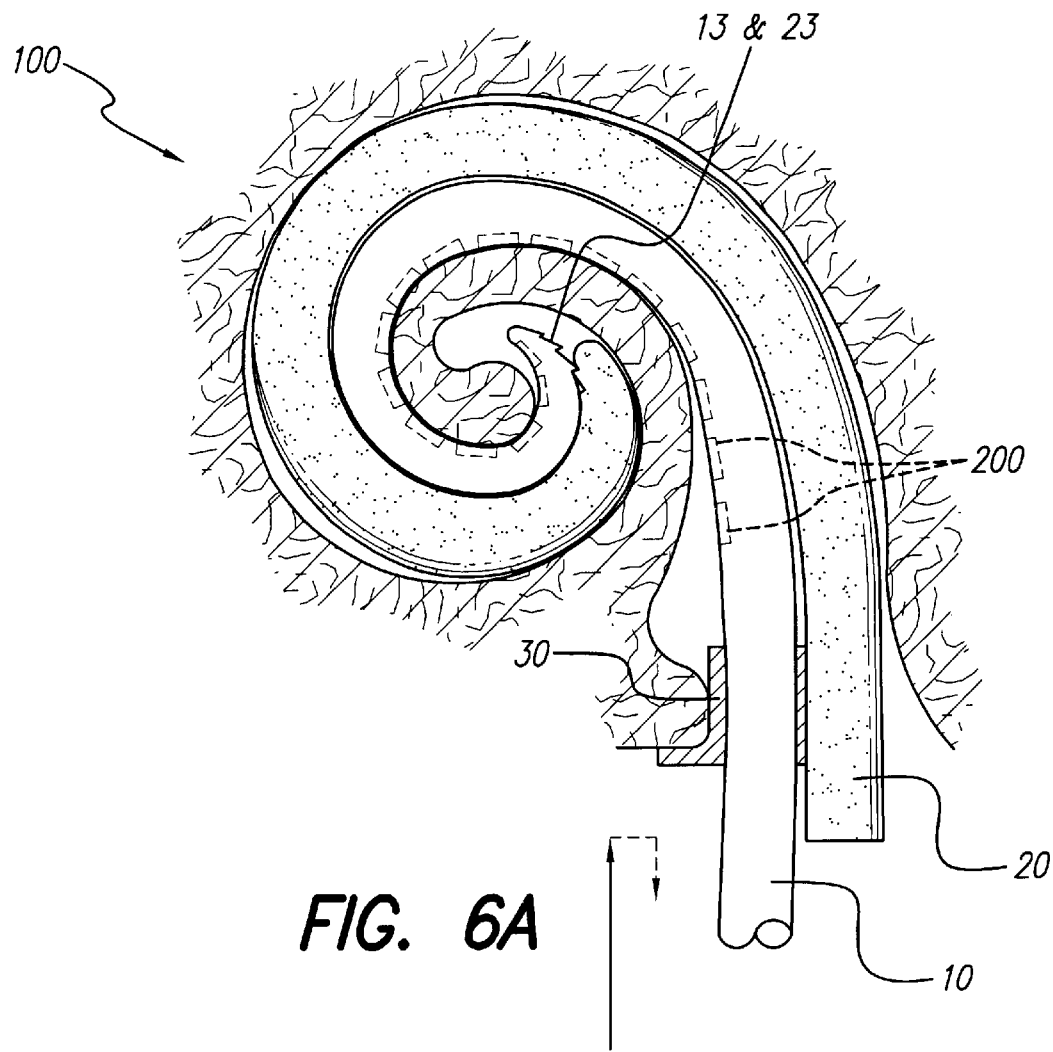
FIG. 6A is a schematic representation of the cochlea as in FIG. 5, but with the electrode array having been inserted into the scala tympani through the electrode-guiding insert.
Figure 6B:
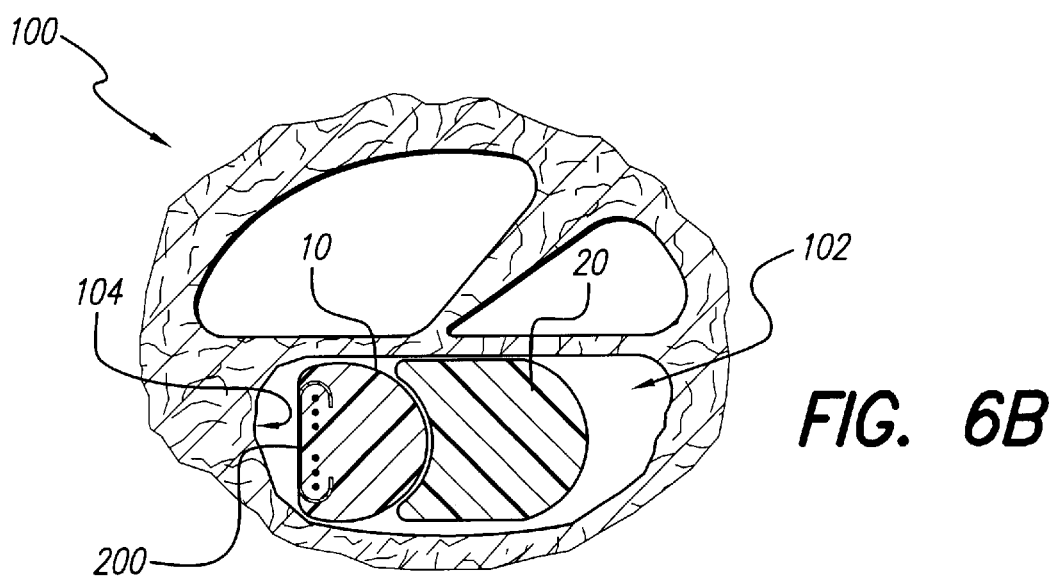
FIG. 6B is a cross-sectional view of the scala tympani of FIG. 6A, showing the manner in which the positioner forces the electrode array to hug the modiolus of the cochlea.

With the positioner 20 and electrode-guiding insert 30, in place, the electrode array 10 is next inserted through the opening 31 of the guiding insert 30 to the desired depth as shown in FIGS. 6A and 6B. Insertion is performed so that the electrodes 200 lie on the inside curve of the electrode array as it is inserted into the cochlea, thereby placing these electrodes 200 adjacent the modiolar wall 104.

The desired depth of insertion is preferably beyond the depth of the positioner 20. Advantageously, because the carrier body 204 of the electrode array 10 is tapered, it may be sized so that the diameter of the opening 31 within the guiding insert 30 effectively prevents further insertion once full insertion has occurred.

As explained above, the distal end portion 11 of the electrode array 10 includes engaging members, e.g., locking teeth or barbs 13, that engage with corresponding engaging members, e.g., teeth or barbs 23, located at the distal end of the positioner 20. Once the electrode array 10 has been inserted, the electrodes 200 are positioned very close to the modiolus of the cochlea, as desired. As a final optimization of the position of the electrode contacts 200 of the electrode array, the electrode array 10 may be pulled back slightly (about 2 mm). This backward motion assures that the distal end portions 11 and 21 of the electrode array 10 and the positioner 20 are engaged by the barbs 13 and 23 located thereon. Such engagement may further serve to force the electrode contacts 200 into close contact, e.g., direct contact, with the modiolar wall.

A preferred method of making the electrode array 10 is described in patent application Ser. No. 09/140,034, now U.S. Pat. No. 6,038,484, which patent is incorporated herein by reference. It is to be emphasized that while the method disclosed in the referenced application is not the only way an electrode array suitable for use with the electrode system of the invention could be made. Rather, it merely represents an easy and inexpensive (and thus a preferred) way in which the electrode array may be fashioned.

Alternative Embodiments

Figure 7A:
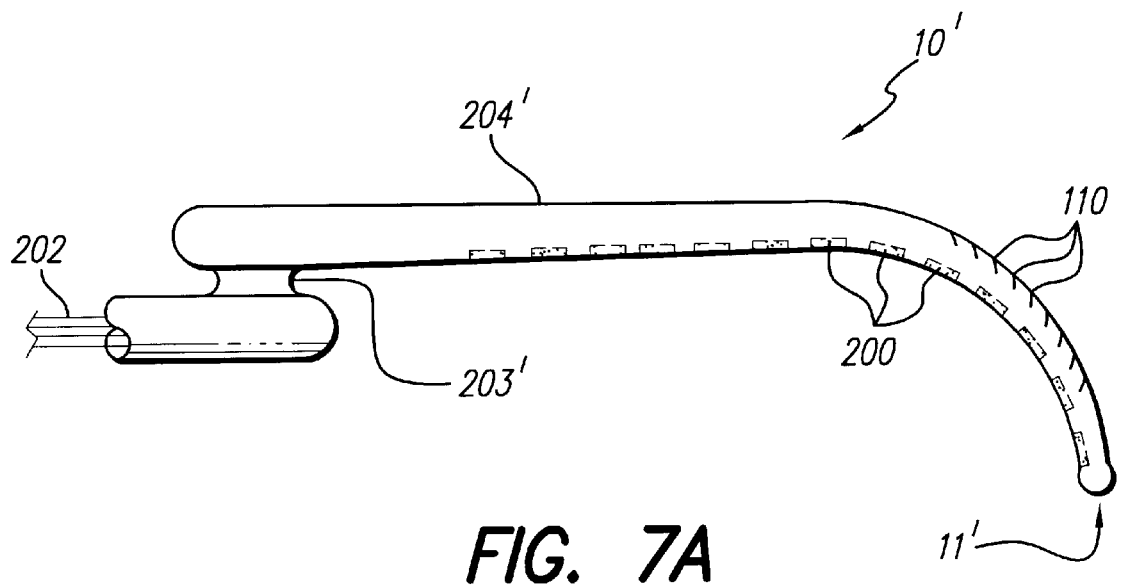
FIG. 7A depicts an alternate embodiment of a curved electrode array that may be used with the present invention.
Figure 7B:
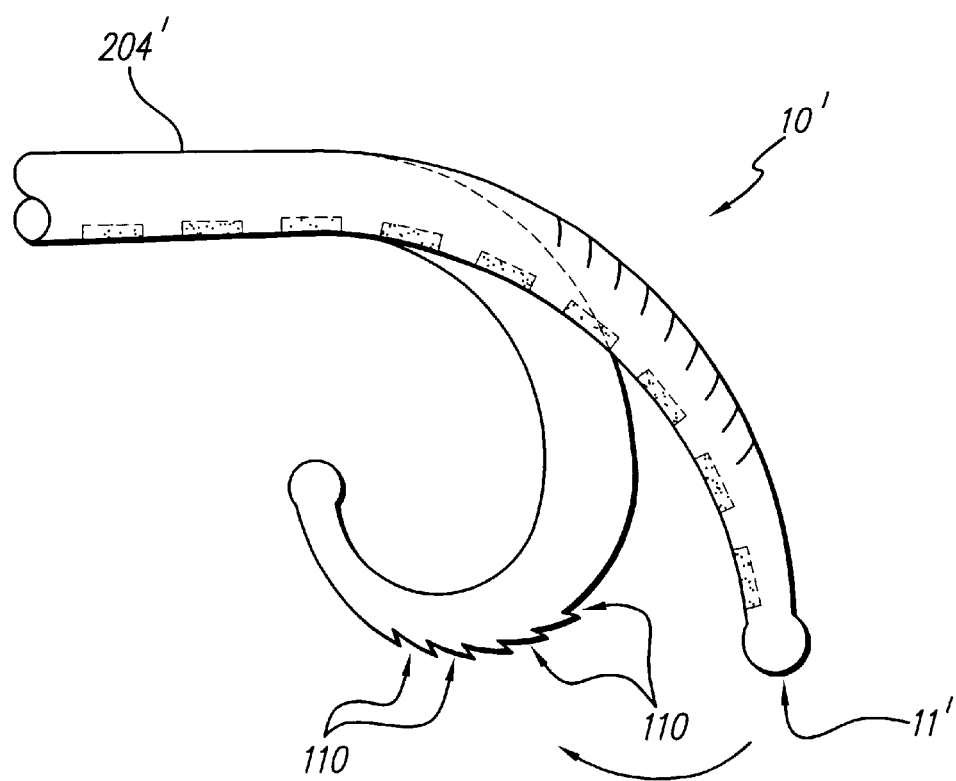
FIG. 7B shows an enlarged view of the distal region of the electrode array of FIG. 7A, and further shows a series of serrations or teeth that are formed along the back side of the electrode array, on a side of the electrode array that is opposite the electrode contacts.
Figure 7C:
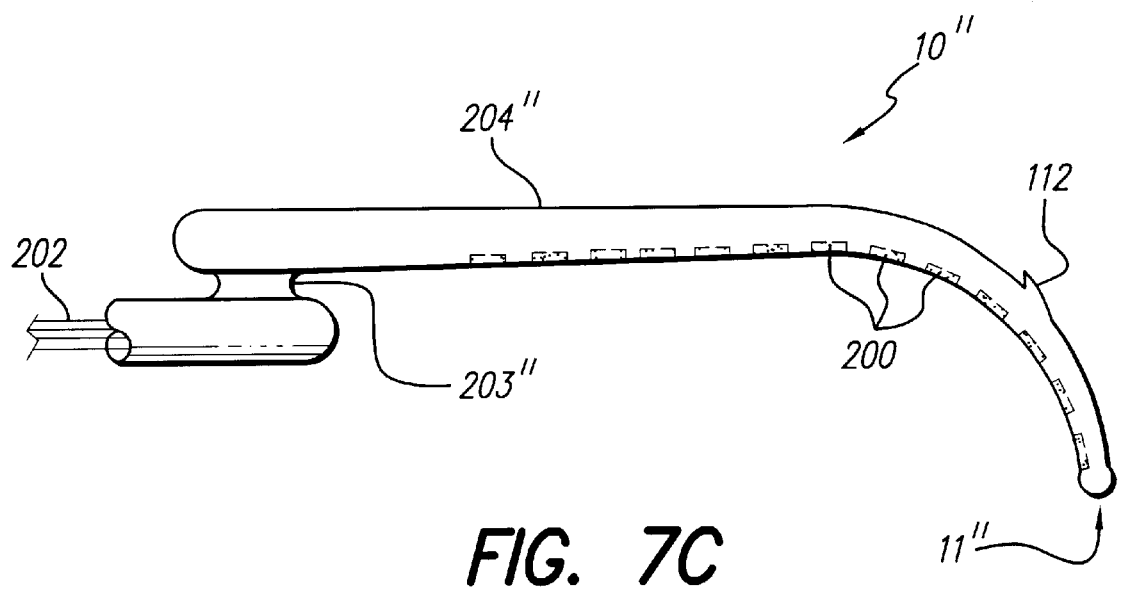
FIG. 7C shows yet another embodiment of a curved electrode array that may be used with the invention.
Figure 7D:
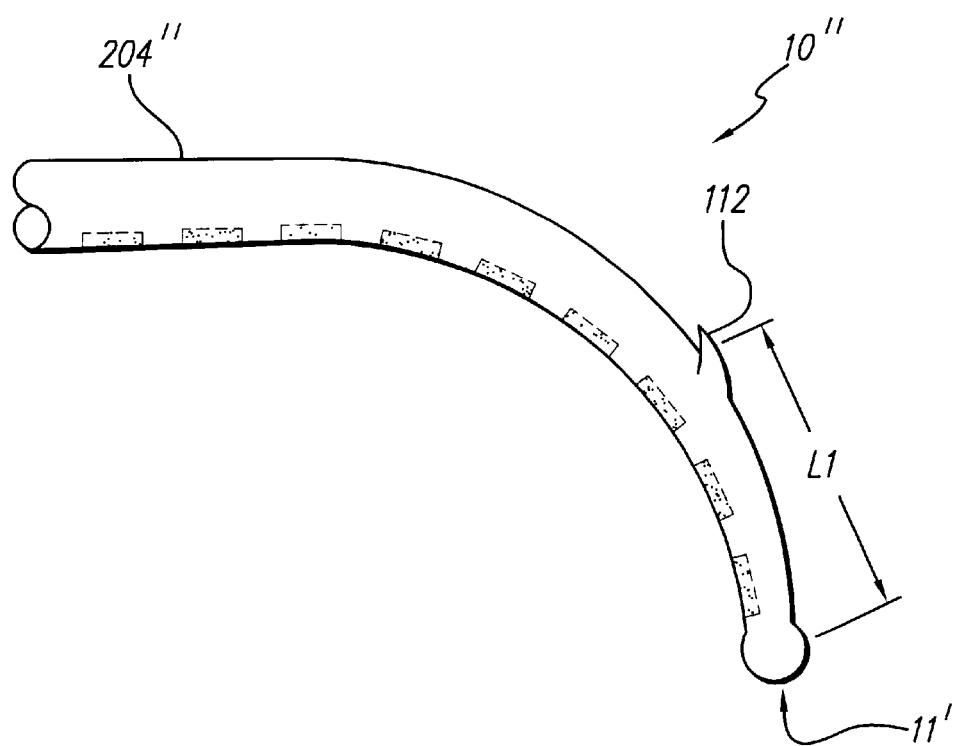
FIG. 7D shows an enlarged view of the distal region of the electrode array of FIG. 7C, and further shows a single engaging flap, serration or tooth that is formed along the back side of the electrode array, on a side of the electrode array that is opposite the electrode contacts.

Other embodiments of the invention may also be used. For example, FIGS. 7A–7D depict two alternative embodiments of the electrode portion of the invention. A first alternative embodiment, designated as "Electrode A" is shown in FIGS. 7A and 7B, as electrode 10'. A second alternative embodiment, designated as "Electrode B" is shown in FIGS. 7C and 7D as electrode 10".

The electrode array 10', shown in FIGS. 7A and 7B, is similar to the electrode array 10, previously described, except that it is generally formed in a curved shape, with the spaced-apart electrode contacts 200 being located on the inside of the curve. Wires 202 connect with each electrode contact 200, and an offset 203' facilitates insertion of the array 10' into the cochlea. The electrode array 10' further includes a soft distal tip 11', typically with rounded, smooth edges shaped in the form of a ball or sphere or hemisphere. The electrode array 10' also includes a plurality of serrations 110 formed in the carrier 204' along its outer edge (the outer edge comprising the edge opposite the electrode edge, i.e., opposite the inner edge located on the inside of the curve on which the electrodes 200 are located). When the electrode array 10' is bent into a tighter curve, as it is when inserted into the cochlea, and as shown in FIG. 7B, each of these serrations 110 opens up, providing a plurality of teeth-like engaging members that may be engaged by a sharp or narrow edge on the positioner, as described below.

The serrations 110, or other similar engaging members, are typically located in a region near, but not at, the distal tip 11' of the electrode array 10'. As seen best in FIG. 7B, such region for the engaging members 110 is preferably located between about the third and sixth electrode contacts 200 of the array, where the electrode contacts 200 are numbered beginning at the distal tip of the array (i.e., the most distal electrode contact is the first electrode, the second-most distal electrode contact is the second electrode, and so on). Typically, this region where the serrations 110 are located is between about 2–7 mm from the distal tip 11' of the electrode array.

The electrode array 10", shown in FIGS. 7C and 7D, is similar to the electrode array 10', described above in FIGS. 7A and 7B, except that it includes a single engaging member 112 located a distance L1 from its distal tip 11", where L1 is about 4–5 mm, rather than a plurality of serrations 110. Thus, as seen in FIGS. 7C and 7D, the electrode array 10" is generally formed in a curved shape, with the spaced-apart electrode contacts 200 being carried or formed within a carrier 204", and being located on the inside of the curve. Wires 202 connect with each electrode contact 200, and an offset 203" facilitates insertion of the array 10" into the cochlea. The electrode array 10" further includes a soft distal tip 11", typically with rounded, smooth edges shaped in the form of a ball or sphere or hemisphere.

The electrode array 10" also includes a single engaging member 112, e.g., a tab or fin 112, formed in the carrier 204" along its outer edge (the outer edge comprising the edge opposite the electrode edge, i.e., opposite the inner edge located on the inside of the curve on which the electrodes 200 are located). When the electrode a array 10" is bent into a tighter curve, as it is when inserted into the cochlea, and as shown in FIG. 7D, this tab or fin 112 opens up, protruding away from the body of the carrier 204", thereby making it easier for a corresponding engaging member, e.g., a sharp or narrow edge, on the positioner to engage therewith, as described below.

Turning next to FIGS. 8A–8D, an alternative embodiment of a positioner 20' adapted for use with the electrode array 10' is illustrated. A perspective view of the entire positioner 20' is shown in FIG. 8B. FIG. BA shows a proximal end view of the positioner 20'; FIG. 8C shows an enlarged perspective view of the distal end of the positioner 20'; and FIG. 8D shows a sectional view of the distal end of the positioner taken along the lines 8D—8D of FIG. 8C.

As seen in FIGS. 8A–8D, the positioner 20' is formed from a suitable silicone polymer in a relatively straight shape, forming an elongate flexible member. The entire positioner is best seen in FIG. 8B. Such flexible member has a distal tip 21' and a proximal end 23'. A first pair of keeper tabs 122, comprising tabs 122a and 122b (sometimes referred to as "keeper wings",or just "wings"), protrude from the positioner in the vicinity of its distal tip 21'. A first tab 122a of the first pair of tabs 122 is adapted to lie against one side of the electrode array 10' near the distal end 11' of the array 10'. The other tab 122b of the first pair of keeper tabs 122 is similarly adapted to lie against an opposite side of the electrode array 10'.The space between the tabs 122a and 122b thus defines a distal channel wherein the distal end of the electrode array 10' may be placed. This distal channel keeps the distal end of the positioner 20' alongside the distal end 11' of the electrode array 10' when the positioner 20' is inserted into the cochlea alongside the electrode array 10', as explained more fully below in conjunction with FIGS. 19A–19E.

A second pair of keeper tabs 123, comprising tabs 123a and 123b (sometimes also referred to as "keeper wings",or just "wings"), protrude from the positioner at a location that is near the location where the first pair of keeper tabs 122 protrude, but closer to the proximal end of the positioner 20'. A first tab 123a of the second pair of tabs 123 is adapted to lie against one side of the electrode array 10', and the other tab 123b of the second pair of keeper tabs 123 is similarly adapted to lie against an opposite side of the electrode array 10'. The space between the tabs 123a and 123b thus further defines the distal channel wherein the distal end of the electrode array 10' may be placed.

In one embodiment, a space L2 of at least 0.5 mm separates a proximal edge of the keeper tab 122a or 122b from a distal edge of the keeper tab 123a or 123b, as depicted in FIG. 8C.

The fist air of keeper tabs 122, as well as the second pair of keeper tabs 123, are formed of the same material as the elongate flexible member that makes up the positioner 20'. As a result, the keeper tab pairs 122 and 123 are also flexible, forming an integral part of the flexible member that makes up the positioner 20'.

The positioner 20' further includes a pair of side walls 126 protruding from a proximal end 23' of the positioner 20'. One side wall 126a of the pair of side walls 126 is adapted to lie against one side of the proximal end of the electrode array 10', and the other side wall 126b of the pair of side walls 126 is adapted to lie against an opposite side of the proximal end of the electrode array 10'. The space between the side walls 126a and 126b thus defines a proximal channel adapted to receive a corresponding proximal end of the electrode array 10'. This proximal channel is adapted to keep the proximal end of the positioner 20' alongside the proximal end of the electrode array 10' when the positioner 20' is inserted into the cochlea alongside, i.e., along the back side of, the electrode array 10'.

A lumen or passageway 120 is formed to pass longitudinally through the body of the positioner 10'. This lumen or passageway 120 is closed at the distal end 21' of the positioner 20', as seen best in the sectional view of FIG. 8D. The lumen or passageway 120 is adapted to receive a stylet wire. The stylet wire is used as part of a tool during the insertion process to facilitate insertion of the positioner 20' into the scala tympani of the cochlea after the electrode array 10' has already been inserted therein, as explained in more detail below in connection with FIGS. 19A–19E.

Included within the distal channel formed between the first and second pair of keeper tabs 122 and 123 of the positioner 20' are engagement members 128. These engagement members 128, in one embodiment, comprise slanting teeth, as seen best in the sectional view of FIG. 8D. These slanting teeth 128 are adapted to engage with the serrations 110 on the back side of the electrode array 10' when the positioner 20' is inserted into the cochlea alongside the electrode array 10'. As such engagement occurs, pushing the positioner 20' deeper into the cochlea also carries the electrode array deeper into the cochlea. Advantageously, however, the positioner 20' may be pulled backward within, or even entirely removed from, the cochlea while still leaving the electrode array 10' deeply inserted within the cochlea. Thus, it is seen that the electrode system provided by this embodiment of the invention, which electrode system includes both the electrode array 10' and the positioner 20', advantageously allows the flexible positioner 20' to be detachably engaged with the distal region of the electrode array during insertion, but which positioner 20' is easily separated, and detached from, the electrode array 10' should the need arise to remove the positioner 20' from the cochlea.

Turning next to FIGS. 8E–8H, another alternative embodiment of a positioner 20" adapted for use with the electrode array 10" is illustrated. A perspective view of the entire positioner 20" is shown in FIG. 8F. FIG. 8E shows a proximal end view of the positioner 20"; FIG. 8G shows an enlarged perspective view of the distal end of the positioner 20"; and FIG. 8H shows a sectional view of the distal end of the positioner taken along the lines 8H—8H of FIG. 8G.

The positioner 20" shown in FIGS. 8E–8H is substantially identical to the positioner 20' described above in connection with FIGS. 8A–8D, with one major exception. That major exception is that the engaging members 128 used on the positioner 20' are not used on the positioner 20". Rather, the positioner 20" relies upon the relatively sharp distal tip 21" of the positioner 20" to function as the engaging member which engages the protruding tab or fin 112 along a back side of the electrode array 10" (see FIG. 7D). Thus, with the exception of the engaging members 128 used with the positioner 20' and the sharp distal tip 21" used with the positioner 20", the description of the positioner 20" is the same as the description of the positioner 20', presented above, and will not be repeated. Corresponding reference numerals are used to describe like components or elements in both the positioner 20' and the positioner 20".

Another minor difference between the positioner 20' shown in FIG. 8C and the positioner 20" shown in FIG. 8G is that the spacing between a promimal edge of the keeper tab 122a or 122b from a distal edge of the keeper tab 123a or 123b for the positioner 20", as depicted in FIG. 8G, is L3, where L3 is about 1.0 mm (rather than the 0.5 mm shown in FIG. 8C). As also represented in FIG. 8G, the tabs 122a and 122b, as well as the tabs 123a and 123b, have a lenght of L4, where L4 is about 1.0 mm. It is to be emphasized, however, that these dimensions are only representative of various dimensions that could be used with either the positioner 20' or the positioner 20", and are not meant to be limiting.

Figure 9A:
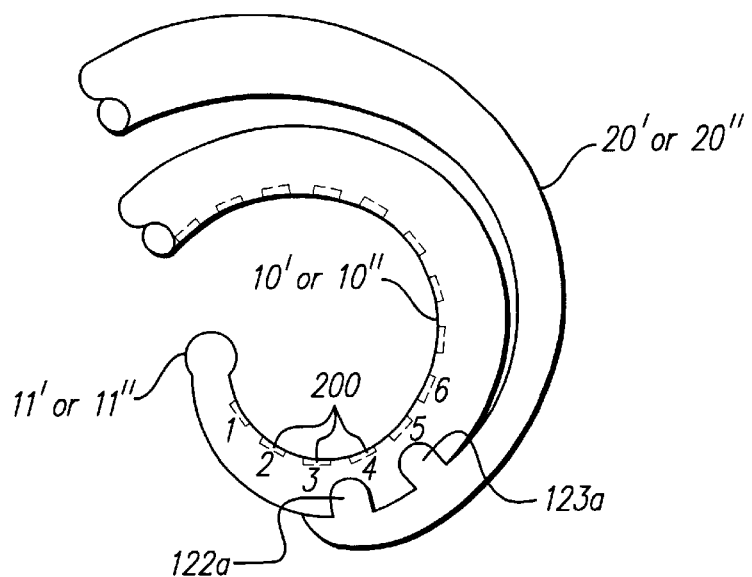
FIG. 9A depicts the desired positioning of the distal portion of the positioner alongside the distal portion of the electrode array.

The desired positioning of the distal portion of the positioner alongside the distal portion of the electrode array, for both the electrode arrays 10' and 10", as well as the positioners 20' and 20", is depicted in FIG. 9A. As seen in FIG.

9A, the keeper tabs 122*a* and 123*a* lie against one side of the electrode array 10' or 10" near its distal tip 11' or 11" at a location that corresponds to about the same location as the third, fourth or fifth electrode contacts 200 (counting from the distal tip 11' or 11"). The other keeper tabs 122*b* and 123*b* (which are not visible in FIG. 9A) lie against the other side of the electrode array 10' or 10".

Figure 9C:
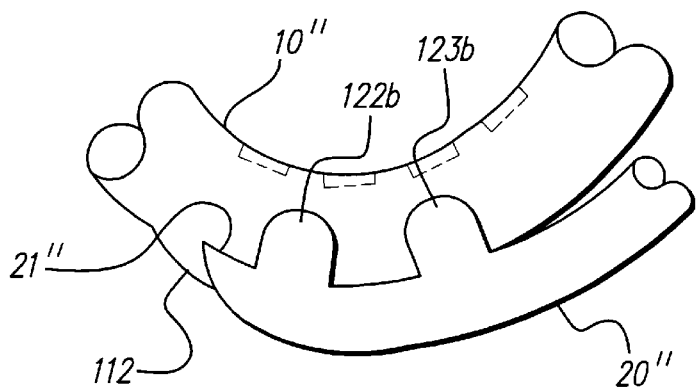
FIG. 9C shows an enlarged view of another embodiment of the engagement between the positioner and the electrode array.
Figure 9B:
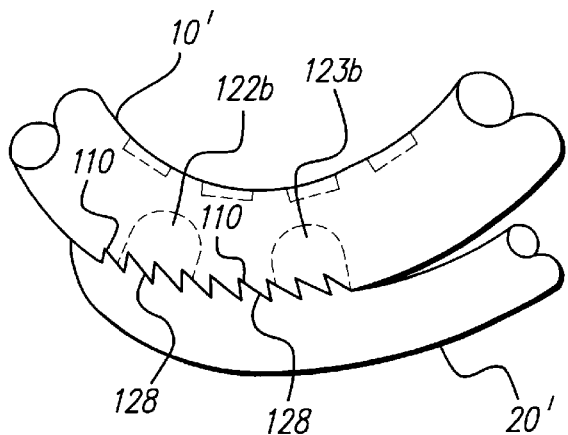
FIG. 9B shows an enlarged view of the engagement between the teeth of the positioner and the engagement members of the electrode array.

FIG. 9B shows the engagement between the teeth 128 of the positioner 20' and the serrations 110, or equivalent engaging members, of the electrode array 10' when the positioner 20' is placed alongside the electrode array 10' as in FIG. 9A.

Similarly, FIG. 9C shows the engagement between the tip 21" of the positioner 20" and the tab or fin 112, or equivalent engaging member, of the electrode array 10" when the positioner 20" is placed alongside the electrode array 10" as in FIG. 9A.

Figure 10:
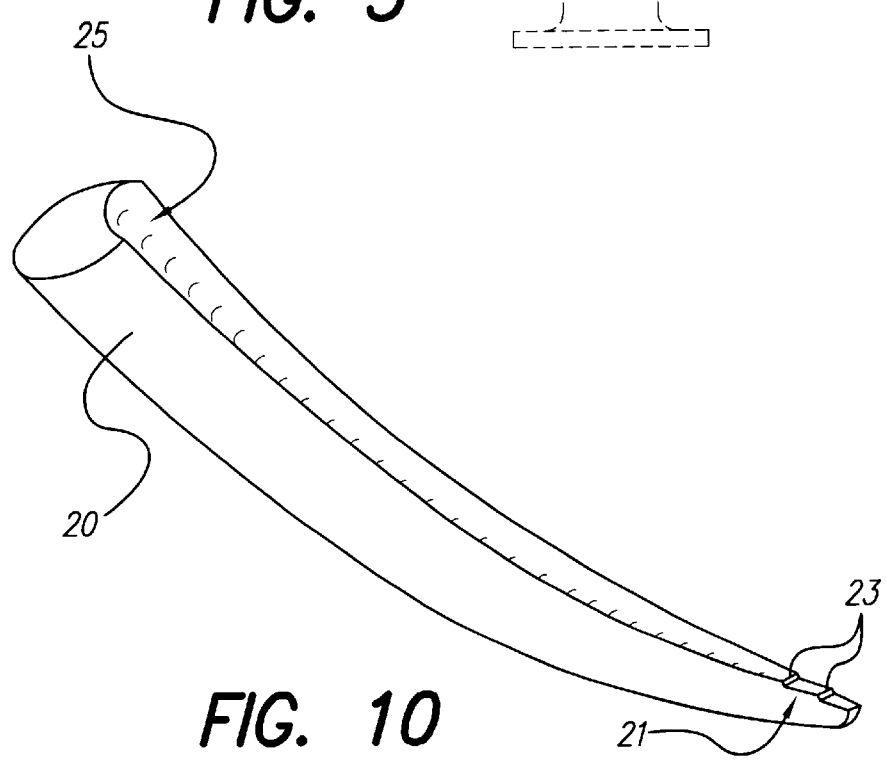
FIG. 10 is a perspective view of yet another embodiment of a positioner that may be made in accordance with the present invention, lying in a somewhat straightened position.

In yet another embodiment of the invention, the positioner 20 assumes a somewhat straightened position, but not as straight as in FIGS. 8B and 8F, and yet not as curved as in FIG. 2A. Such an intermediate curved embodiment is shown in FIG. 10. The positioner 20 shown in FIG. 10 may be used with any type of electrode system or electrode array in order to help position the electrode contacts of the array in a desired position within the cochlea. When so used, the positioner may be inserted into the cochlea first (i.e., before insertion of the electrode array), as described above in connection with FIGS. 4A and 4B, or second (i.e., after insertion of the electrode array), as described more fully below.

Typically, as indicated above, the positioner 20 is curved as illustrated in FIGS. 2A, 2B and 2C, although the degree and amount of curvature is not critical given the flexible nature of the positioner. The distal end of the positioner 20 may include a plurality of barbs or bumps 23 formed therein. Moreover, the positioner 20 may include a smooth groove or channel 25 located along one side thereof to facilitate holding the electrode array 10 on that side of the positioner facing the modiolar wall. This channel or groove 25, when used, traverses the entire length of the positioner 20, or at least the length of the positioner up to the distal tip where the barbs or bumps 23 may be located.

As described above, the flexible positioner 20 is preferably made from a silicone polymer, and is molded to assume a generally curved shape, with a width or cross-sectional area that is tapered, as required, to match the cross-sectional area or width of the scala tympani of the cochlea. Preferably, the radius. of curvature "R" of the positioner 20 is selected to be somewhat larger than the natural curvature of the scala tympani of the cochlea. That is, when inserted into the scala tympani, the positioner 20 ideally assumes a tighter wind or coil than that afforded by its formed curved shape. This assures that when inserted into the scala tympani, the positioner 20 is held away from the modiolar wall 104, leaving a cavity or channel 22 against the modiolar wall 104 wherein the electrode array 10, 10' or 10", or any other type of electrode array, may be inserted. Further, this preferred shape and positioning of the positioner within the cochlea improve the directional stability of the electrode array during insertion, i.e., help prevent rotation of the electrode array, thereby assuring that the electrode contacts remain positioned adjacent the modiolar wall.

Figure 11:
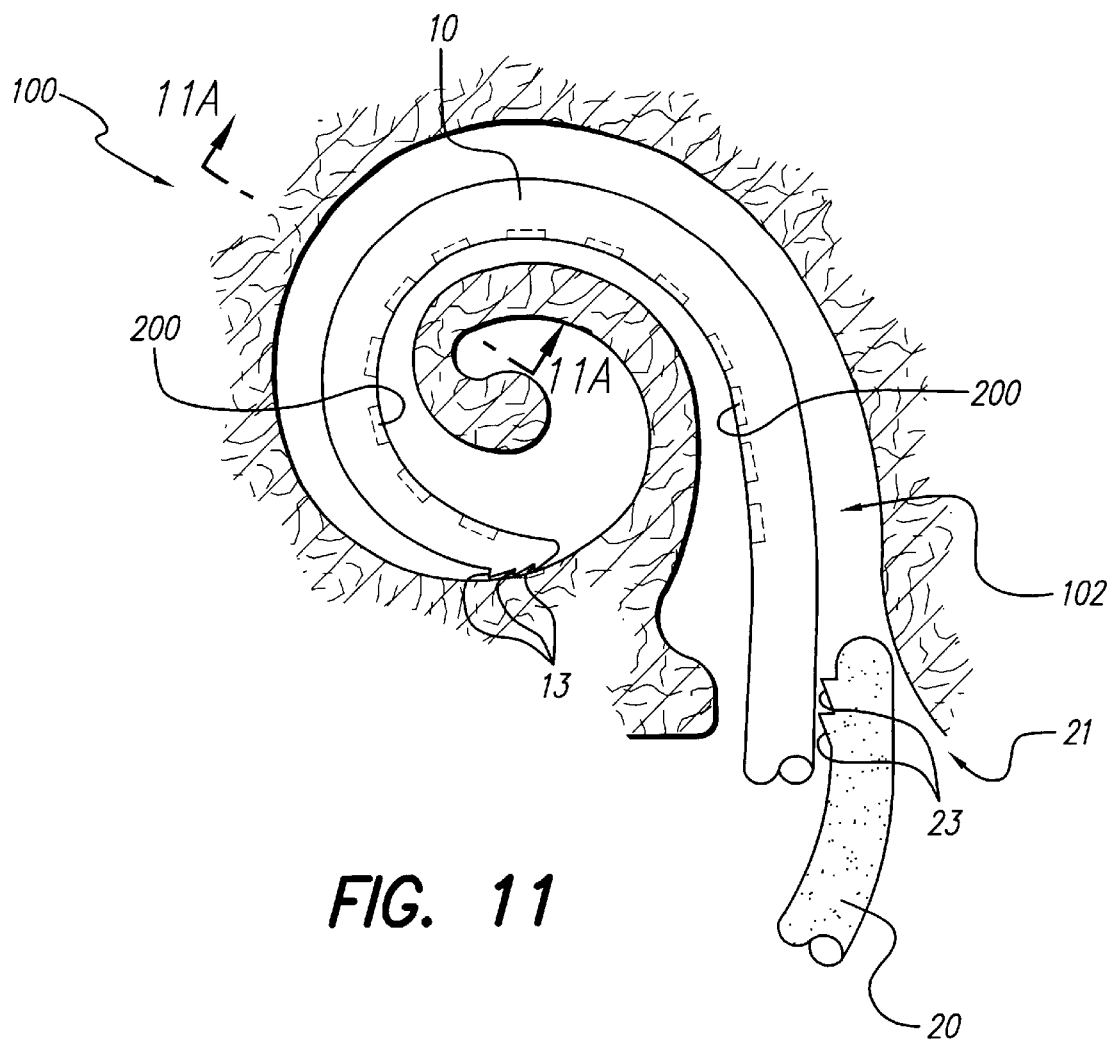
FIG. 11 is a schematic representation of the cochlea showing an alternate technique for insertion of the electrode array, and in particular showing the electrode array first inserted into the cochlea and showing the positioner inserted second into the cochlea.

One technique for inserting an electrode array 10 into the cochlea without having to use a guiding insert 30 is to first insert the electrode array 10 into the cochlea using any desired technique, as shown in the FIG. 11. Typically, during such insertion, the electrode contacts 200 of the electrode array 10 will be oriented to face the desired wall within the cochlea, e.g., the modiolar wall 104.

Figure 11A:
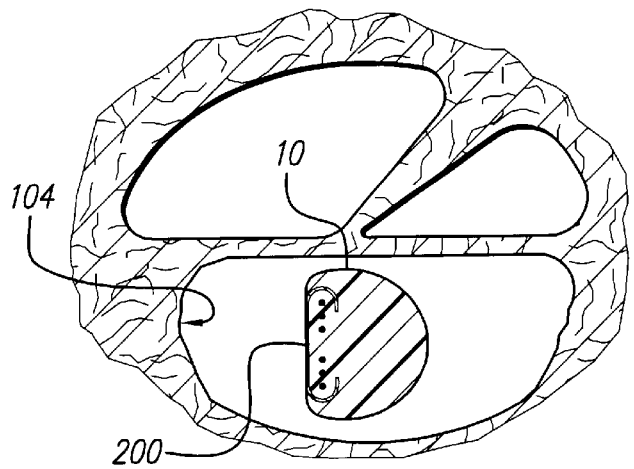
FIG. 11A is a sectional view taken along the line 11A—11A of FIG. 11.

As evident from the schematic representation of FIG. 11, as well as the sectional view of FIG. 11A, the electrode contacts 200 of the electrode array 10, when the electrode array 10 is first inserted into the cochlea are not firmly held in position against the inner wall (modiolus) of the cochlea 100. In order to position or hold the electrode contacts 200 up against the modiolar wall, the positioner 20 is also inserted into the cochlea, behind and alongside the electrode array 10, i.e., on the side of the electrode array 10 farthest from the modiolus, as seen in FIG. 11 (which shows the distal tip 21 of the positioner 20 just as it is first inserted behind the electrode array 10 within the cochlea).

Figure 12:
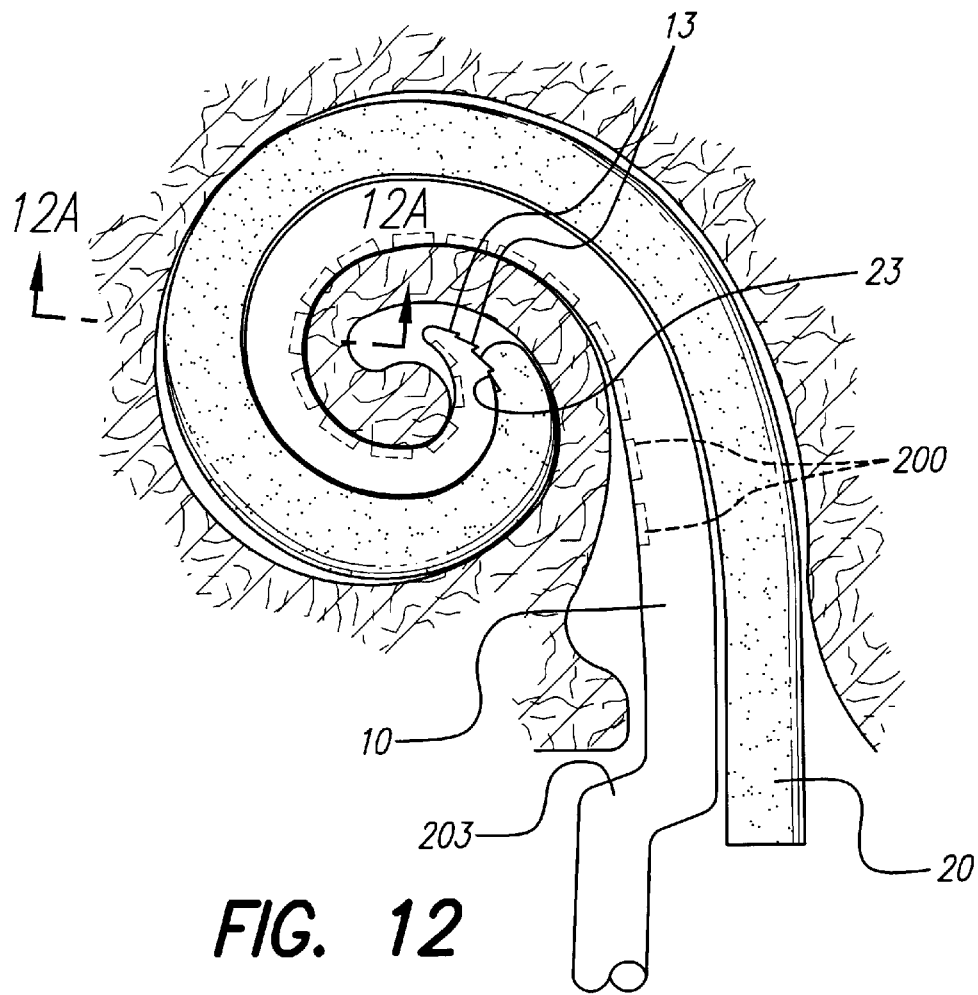
FIG. 12 is a schematic representation of the cochlea as in FIG. 11, but showing the positioner fully inserted into the cochlea.
Figure 12A:
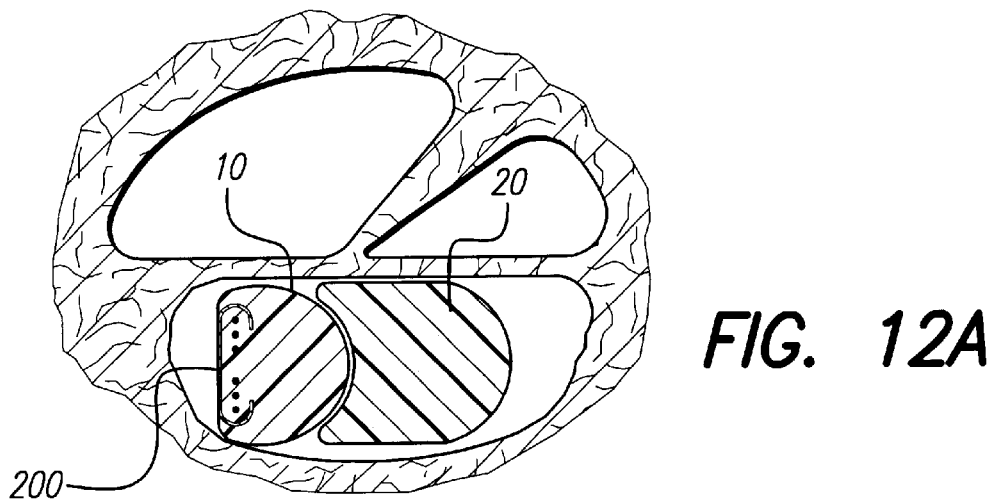
FIG. 12A is a sectional view of the cochlea taken along the line 12A—12A of FIG. 12.

As the positioner is pushed deeper into the cochlea, it forces the electrode array 10 up against the modiolar wall 104, which action causes most, if not all, of the electrode contacts 200 to be in direct or nearly direct contact (touching) the modiolar wall. Moreover, as the positioner 20 is pushed still deeper into the cochlea, it eventually grabs or engages with (either through a friction fit, and/or with the assistance of the barbs or bumps 23) the electrode array 10 and carries the electrode array 10 with it deeper into the cochlea, causing the electrode array 10 to be inserted, e.g., an additional ½ turn deeper into the cochlea than when initially inserted. Advantageously, once in such fully inserted position, as shown in FIGS. 12 and 12A, the barbs or bumps 23 on the positioner, in combination with the barbs, teeth or other engaging members 13 on the electrode array, prevent the electrode array 10 from sliding backwards out of the cochlea, yet allow the positioner, if needed, to be removed from the cochlea.

Note, typically the electrode array 10, as seen best in FIG. 1A, has an offset 203. Such offset 203 functions as a stop to prevent the electrode array from being inserted too deep into the cochlea. Even when such offset cannot effectively function as a stop, it can always function as a mark, to aid the physician to know when the desired insertion depth has been achieved.

Figure 15E:
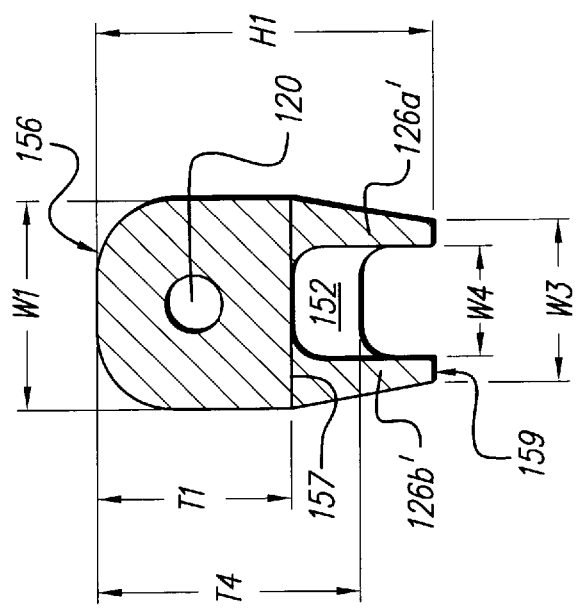
FIG. 15E is a sectional view of the positioner of FIG. 15A taken at its proximal end along the line 15E—15E.
Figure 13:
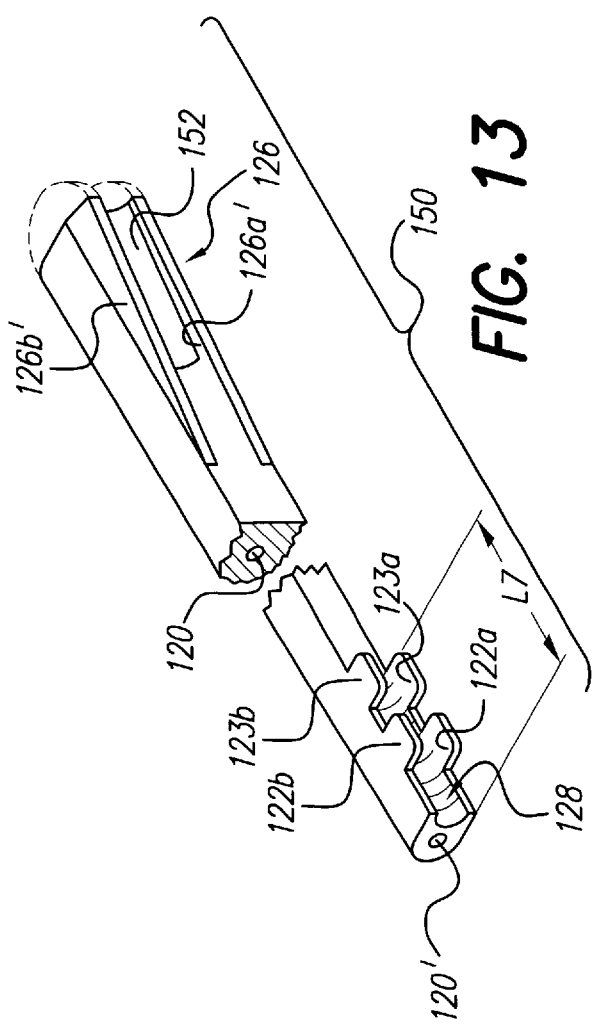
FIG. 13 shows the proximal and distal end regions of yet a further embodiment of a positioner that may be used with the invention.

Turning next to FIGS. 13, 14A, 14B, and 15A–15E, there is shown another variation of a positioner 150 that may be used with the cochlear electrode system of the present invention. In these figures, FIG. 13 shows a broken perspective view of the distal and proximal ends of the positioner 150; FIGS. 14A and 14B show a bottom view of the proximal and distal ends of the positioner, respectively, looking into the electrode channel created by the proximal side walls and distal keeper tabs; FIGS. 15A and 15B show a side cross sectional view of the proximal and distal ends of the positioner 150, respectively; and FIGS. 15C, 15D and 15E are sectional views taken along the lines 15C—15C, 15D—15D, and 15E—15E in FIGS. 15A and 15B. Representative dimensions (expressed in millimeters) of the positioner 150 are specified throughout the specification. It is to be understood, however, that these dimensions are only representative of typical dimensions that may be used during the manufacture of the positioner 150, and are not intended to be limiting, except to the extent that such dimensions are present in the claims.

It should also be understood that the positioner 150 may be made from any suitable biocompatible material using techniques known in the art. Typically, the positioner 150 will be made using conventional molding techniques from a silicone polymer. A suitable silicone polymer is commercially available under the name LSR-25 or LSR-70, which vary in degree of softness and flexibility, where LSR-70 is not as soft nor as flexible as LSR-25.

As seen in FIGS. 13, 14A, 14B, and 15A–15E, the positioner 150 is similar to the positioners 20' and 20", previously described, except for a few notable differences. Those elements or components of the positioner 150 that are the same as those elements or components of the positioners 20' and 20", previously described, are referred to using the same or similar reference numerals, and a further description of those common components will not be repeated.

The primary differences between the positioner 150 and the positioners 20' and 20", previously described, relate to the presence of a sloping floor 152 in the bottom of the electrode channel located between the side walls 126 at the proximal end of the positioner, the shape and general orientation of the proximal side walls 126, and the number and dispersement of the engaging members 128 located at the distal end of the positioner. Other minor differences also exist as shown in the drawings.

As seen best in FIGS. 13 and 15A, the pair of proximal side walls 126, comprising a right side wall 126a' and a left side wall 126b' (as viewed in FIG. 15E), have a varying height that, when viewed in the side view of FIG. 15A causes an upper edge of each side wall to slope from a maximum height at the extreme proximal end of the positioner (at sectional line 15E—15E in FIG. 15A) to a zero height, or near zero height, at a distal most location, shown in FIG. 15A as point 154. The length of the side walls, for the embodiment shown in FIG. 15A, from the sectional line 15E—15E to the point 154 is L5, where L5 is approximately 7.0 mm. The maximum height, H1, of the side walls, as seen best in FIG. 15E, and as measured from a top side 156 of the positioner is about 1.70 mm.

The overall thickness T1 of the positioner 150 at the proximal end of the positioner, i.e., at the sectional line 15E—15E, as measured from the top side 156 of the positioner to a bottom side 157 of the positioner, as best seen in FIG. 15E is approximately 0.90 mm. This thickness narrows towards the distal end of the positioner, as seen best in the sectional views of FIGS. 15C and 15D. That is, as seen in FIG. 15D, the thickness T2 of the positioner at the distal end of the positioner, i.e., at sectional line 15D—15D, is approximately 0.5 mm; whereas as seen in FIG. 15C, the thickness T3 of the positioner near the mid-point of the positioner, i.e., at sectional line 15C—15C, is approximately 0.6 mm. Thus, it is seen that the thickness of the positioner tapers from approximately 0.90 mm at its proximal end to about 0.5 mm at its distal end.

The width of the positioner, as measured from its left side to its right side also tapers, as evident from FIG. 15E (proximal end) and FIG. 15D (distal end) from approximately W1=1.10 mm at the proximal end to about W2=0.70 mm at the distal end.

As illustrated best in FIGS. 13, 15A and 15E, the channel formed between the side walls 126a' and 126b' has a sloping floor 152 therein. At the proximal end of the positioner 150, i.e., at the sectional line 15E—15E, the floor 152 is spaced approximately a distance T4, where T4 is about 1.30 mm from the top side 156 of the positioner. This floor, for the embodiment shown in FIGS. 13, 15A and 15E linearly slopes down to the bottom side 157 of the positioner at a point 158, located a distance L6, where L6 is about 3.0 mm distally from the sectional line 15E—15E (see FIG. 15A). The function of the floor 152 is to assure that the electrode array, when placed into the proximal channel located between the side walls 126, is nudged or positioned against the modiolar wall of the cochlea more than it would be without the floor, thereby helping to maintain modiolar-wall contact, or near contact, at the basal end of the scala tympani (near the round window. The floor 152 also functions as a soft wedge to help firmly maintain the positioner and electrode array in their desired positions within the scala tympani.

As further seen best in FIGS. 14A and 15E, the side walls 126 of the positioner 150 have exterior walls that are thicker near the bottom 157 of the positioner 150 than they are at a top edge 159. That is, as seen in FIG. 15E, the width, W1, of the positioner is about 1.10 mm at the proximal end (at section line 15E—15E) of the positioner, and this also is the distance between the exterior edges of the side walls 126 at a base of the side walls (i.e., at point 157). At the top edge 159 of the side walls, however, the distance, W3, between the exterior edges of the side walls 126 narrows to about 0.85 mm. The distance, W4, between the interior walls of the side walls 126, however, does not change from the base to the top, this distance remaining at about 0.60 mm.

FIG. 13 shows the engaging members 128 of the positioner 150 to spread over a distance L7 that extends from the extreme distal tip of the positioner 150 through second pair of keeper tabs 123. Alternatively, as seen in FIG. 14B, the engaging members 128 may be dispersed over a smaller distance L8 that does not extend all the way to the distal tip.

FIG. 13 also shows the hole or passageway 120 that passes through the positioner 150. During manufacture, the hole or passageway 120 will typically pass all the way through the positioner to the distal end of the positioner, where it is shown as hole 120'. At the distal end, the hole 120' is typically plugged with a suitable material, e.g., LSR 25, so that a stylet wire, when inserted into the passageway 120, will not exit through the distal end of the positioner.

The engagement members 128 are typically slanting teeth or ridges as previously described. However, any suitable engaging member 128 may be used that is adapted to engage with corresponding or mating engagement members positioned on the electrode array as the positioner 150 is inserted into the scala tympani after the electrode array has been inserted therein.

Turning next to FIGS. 16, 17, 17A, 17B and 17C, a further embodiment of a positioner 160 is illustrated. In most respects, the positioner shown in FIGS. 16, 17, 17A and 17C is the same as that described previously, and like reference numerals are used to described like components or elements. Hence, only the differences between the positioner 160 and the positioner 150 will be described. FIG. 16 is a broken bottom view of the positioner 160, showing its proximal and distal end regions. FIG. 17 is a side sectional view of positioner 160 taken along a longitudinal center line 172 of FIG. 16; and FIGS. 17A, 17B and 17C are sectional views taken along the sectional lines 17A—17A, 17B—17B, and 17C—17C, respectively, of FIG. 16.

One difference between the positioner 160 and the positioner 150 is the use of a platinum marker element 170 that is placed within the passageway 120 near the distal end of the positioner. Such marker 170 allows the location of the distal tip of the positioner to be easily detected using conventional imaging equipment, e.g., an X-ray machine. The passageway 120 is plugged with a suitable substance, such as LSR-25, at the distal end of the positioner.

Another difference between the positioner 160 and the positioner 150 is that the first pair of keeper tabs 122 used with the positioner 160 are located right at the distal tip of the positioner, rather than spaced back from the distal tip a small distance.

Yet another difference between the positioner 160 and the positioner 150 is that the engagement members 128 used with the positioner 160 are only placed in the region between the keeper tabs 122 and 123, rather than dispersed over a distance L7 or L8, as with the positioner 150.

A further difference between the positioner 160 and the positioner 150 is that the proximal side walls 126 used with the positioner 160 are straight. That is, as seen best in FIG. 17C, a right side wall 126a" and a left side wall 126b" have exterior and interior surfaces that are straight, and the thickness of these walls does not narrow, as is the case of the side , walls 126a' and 126b' used with the positioner 150.

An additional difference between the positioner 160 and the positioner 150 is that a floor 152' of the positioner 160, between the side walls 126a" and 126b", slopes at a relatively steep angle, α, e.g., a 45° angle as shown in FIG. 17, beginning at a point 158', a distance L9, where L9 is only about 2.0 mm from the proximal end (section line 17C—17C).

Turning next to FIGS. 18A, 18B and 18C, a guiding insert 180, also referred to as an insertion tube, is described. A side or profile view of the insert 180 is shown in FIG. 18A, a bottom view is shown in FIG. 18B and an end view is shown in FIG. 18C. The insert 180 functions as a tool to help insert the positioner into the scala tympani after the electrode has been inserted therein, as described more fully below in connection with FIGS. 19A–19E.

The insert 180 comprises a channel, or trough, made from a suitable biocompatible material, such as stainless steel. In one embodiment, the insert 180 may be made from hypodermic stainless steel tubing. The material is cut or formed to create a channel 182, or trough, into which the positioner 10', 10", 150 or 160 may be placed. Right and left side flanges 184 extend to form a deep trough at a distal end of the insert 180. As will be evident from FIG. 19C, below, these side flanges 184 are sufficiently long to position both the electrode array and positioner in the desired position when the positioner is being inserted alongside the electrode array. A stop 186, or lip, is also formed near the distal end of the insert to limit the distance that the distal end of the insert 180 may be inserted into the cochlea, i.e., into the scala tympani of the cochlea.

The insert 180 is made from two half-tube elements 188 and 189 that are joined together using any suitable fastening or joining technique, such as spot welding. The stop 186 is formed at a distal end of the element 189. A proximal end 190 of the member 189 comprises a tube, with a first slit 191 and a second slit 192, orthogonal to the first slit, formed therein.

Figure 19A:
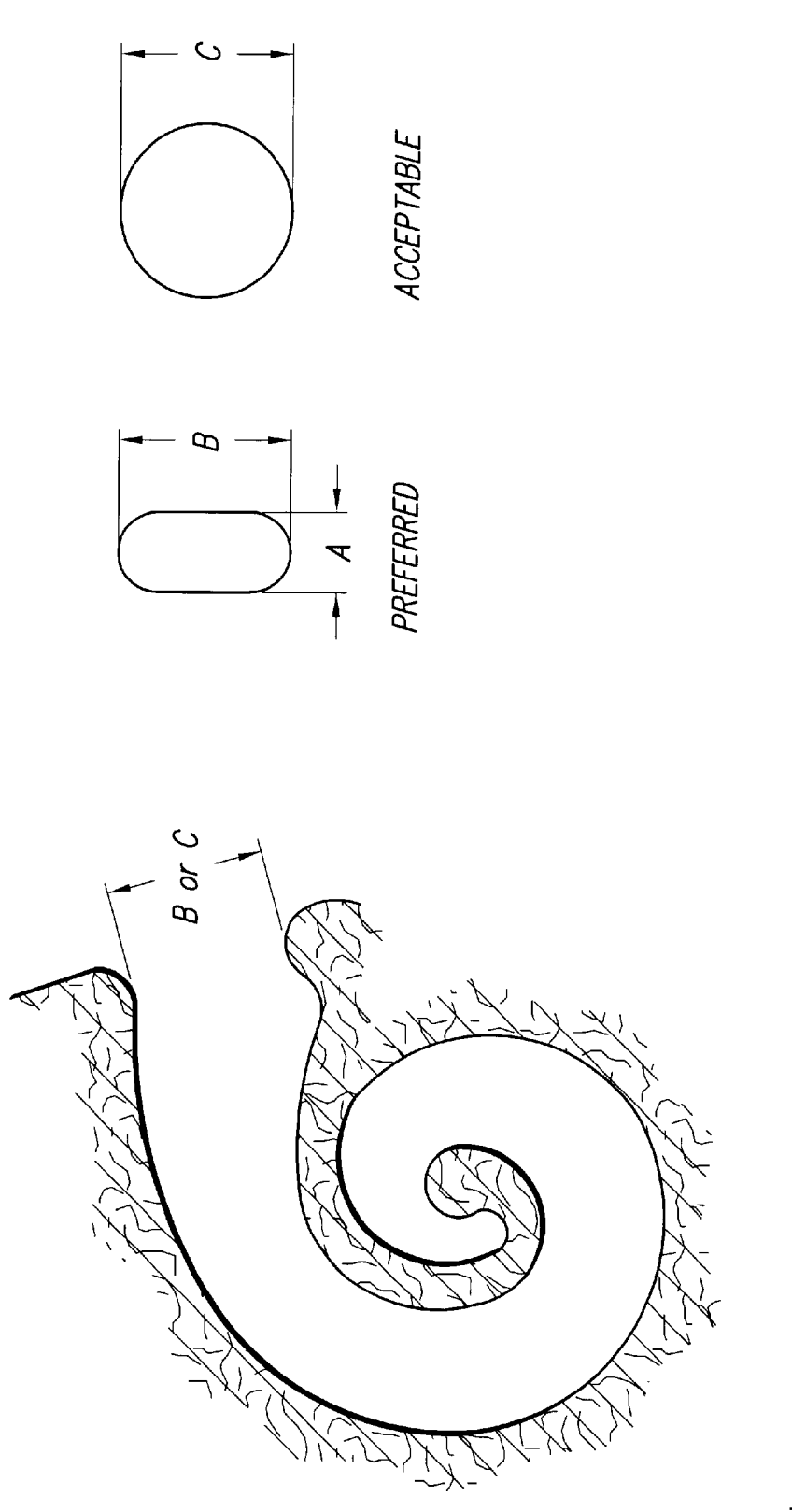

Next, with reference to FIGS. 19A–19E, the method of inserting the electrode system of the present invention will be described. As a first step, shown in FIG. 19A, a cochleostomy is drilled to open up access to the scala tympani of the cochlea. As seen in FIG. 19A, a preferred shape of the opening or hole created by the cochleostomy is an oval shape, having dimensions A and B, where A is about 1.5 mm wide, and B is about 2.0 mm long. Alternatively, a round hole may be made by the cochleostomy having a diameter, C, where C is approximately 2.0 mm.

Figure 19B:
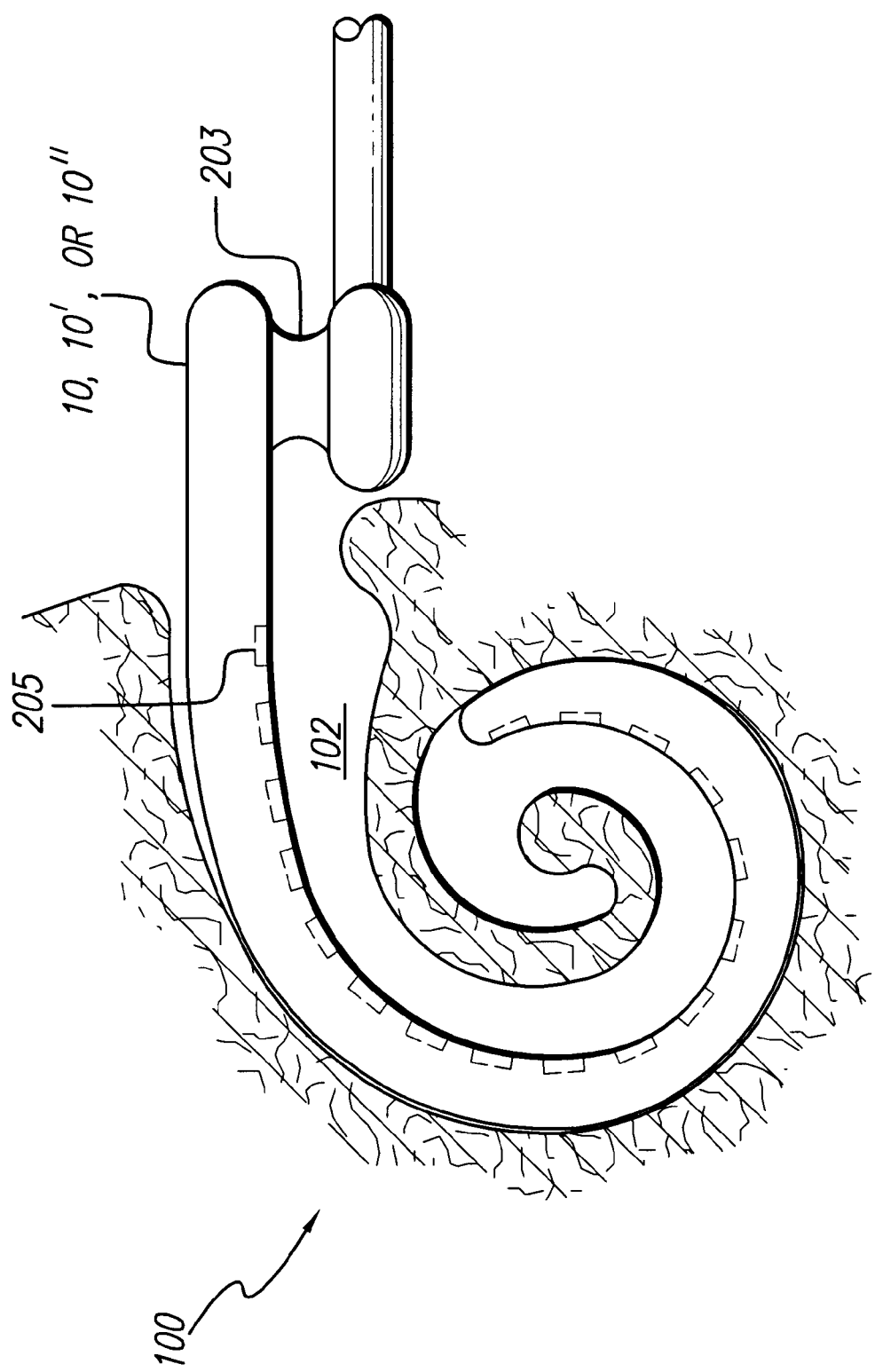

Next, the electrode 10, 10' or 10" is inserted into the scala tympani through the drilled cochleostomy, as shown in FIG. 19B. Some embodiments of the electrode may employ a marker contact 205 near the proximal end of the electrode to mark the proper insertion depth of the electrode. Other embodiments of the electrode may alternatively or conjunctively rely upon the offset 203 as a soft stop that indicates when the electrode has been inserted into the scala tympani 102 to the proper depth. As seen in FIG. 19B, when first inserted into the scala tympani, the electrode typically assumes a position against a rear wall of the scala tympani 102 ((farthest from the modiolar wall 104 of the cochlea).

Figure 19C:
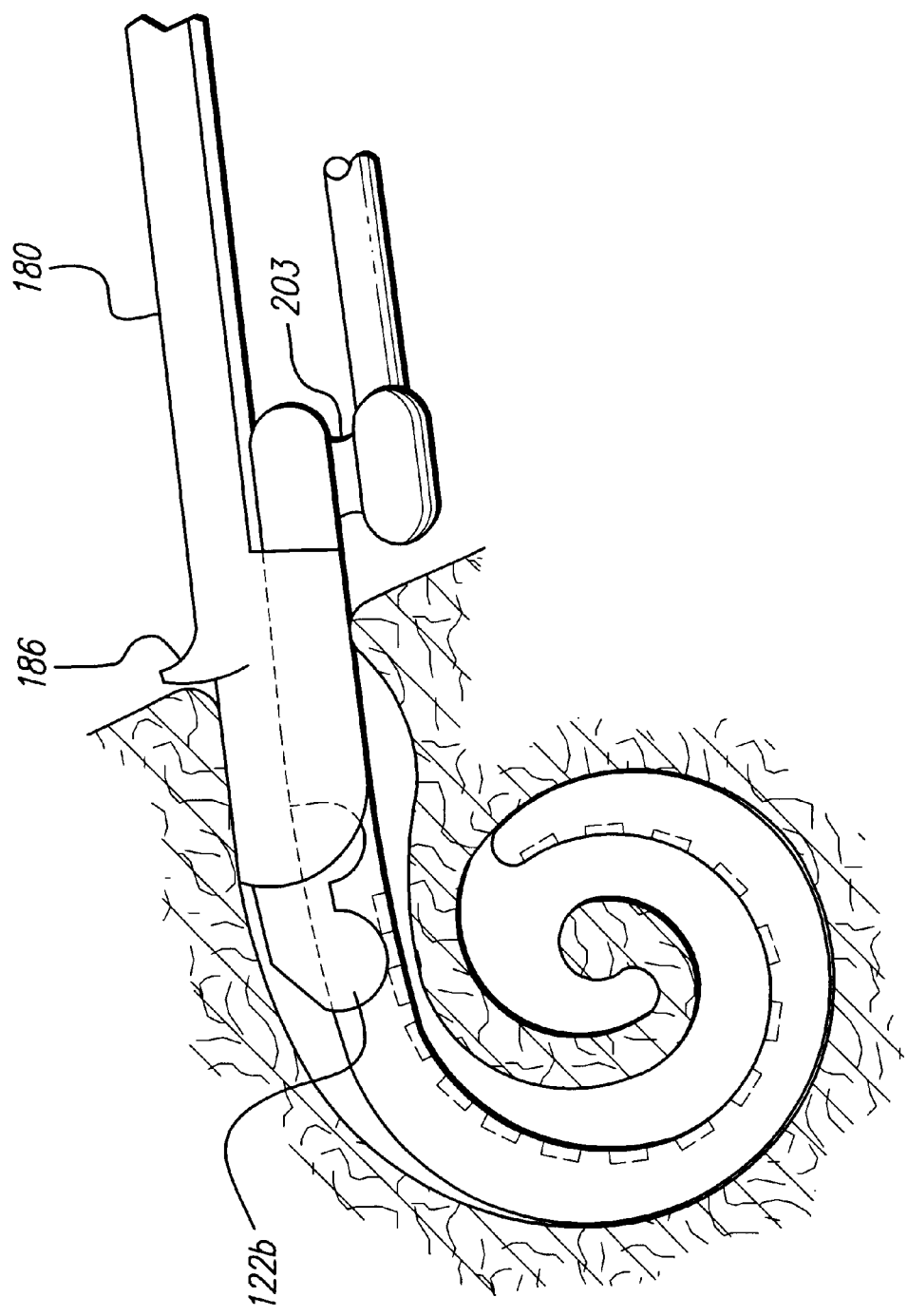

After the electrode has been inserted into the cochlea, the positioner is loaded into the insertion tube 180 (or insert 180) by laying the body of the positioner in the channel or trough 182, with the distal end of the positioner placed near a distal end of the insert 180, and with the keeper tabs 122 and 123 being pointed to go over the electrode array. Then, with the positioner loaded in the insertion tube 180, the distal tip of the insertion tube 180 is placed behind and over the electrode until the stop 186 rests against the edge of the cochleostomy, as shown in FIG. 19C. Then, as shown in FIG. 19D, the positioner is pushed distally, into the scala tympani, until the positioner stops. The insertion tube 180 is then removed, leaving both the electrode array and positioner firmly in place within the scala tympani, as shown in the cochleostomy view of FIG. 19E.

As described above, it is thus seen that the present invention provides a cochlear electrode system that includes a detachable positioner. Such system allows the electrode array to be positioned and maintained against or near the modiolar wall of the cochlea, which is a desired position for effective stimulation.

While the invention herein disclosed has been described by means of specific embodiments and applications thereof, numerous modifications and variations could be made thereto by those skilled in the art without departing from the scope of the invention set forth in the claims.

What is claimed is:

1. A cochlear electrode system comprising:
    an electrode array comprising
        a first elongate flexible carrier having a distal end and a proximal end adapted to be inserted into a human cochlea,
        a plurality of spaced-apart contacts carried by the flexible carrier,
        a plurality of wires carried within the flexible carrier, at least one wire of the plurality of wires being electrically connected to one of the plurality of electrode contacts, each of the plurality of wires having a proximal end that may be coupled to electronic circuitry, and
        a first engagement member on the flexible carrier near the distal end of the electrode array; and
    a positioner comprising
        an elongate flexible member having a distal tip and a proximal end adapted to be inserted into the human cochlea alongside the electrode array,
        a second engagement member on the flexible member near the distal tip of the positioner, wherein the second engagement member is detachably engageable with the first engagement member of the electrode array when the positioner is inserted into the cochlea alongside the electrode array;
        wherein the positioner further has a first pair of keeper tabs protruding from the flexible member in the vicinity of the second engagement member, and wherein one tab of the first pair of keeper tabs is adapted to lie against one side of the electrode array, and the other tab of the first pair of keeper tabs is adapted to lie against an opposite side of the electrode array, to thereby keep the distal end of the positioner alongside the distal end of the electrode array when the positioner is inserted into the cochlea.

2. The cochlear electrode system of claim 1 wherein the positioner has a second pair of keeper tabs protruding from the flexible member near the first pair of tabs, wherein one tab of the second pair of keeper tabs is adapted to lie against one side of the electrode array, and the other tab of the second pair of keeper tabs is adapted to lie against an opposite side of the electrode array, to thereby further keep the distal end of the positioner alongside the distal end of the electrode array when the positioner is inserted into the cochlea.

3. The cochlear electrode system of claim 2 wherein the tabs of the first and second pair of tabs a re flexible, forming an integral part o f the flexible member.

4. The cochlear electrode system of claim 2 wherein a space of at least 0.5 mm separates a proximal edge of the tabs of the first pair of keeper tabs from a distal edge of the tabs of the second pair of keeper tabs.

5. The cochlear electrode system of claim 4 wherein the first pair of keeper tabs is locate d a distance of no more than about 1.0 mm from the distal tip of the positioner.

6. The cochlear electrode system of claim 4 wherein a distal edge of the tabs of the first pair of keeper tabs is located at the distal tip.

7. The cochlear electrode system of claim 6 wherein the distal tip of the positioner is formed to define a frontal edge of the positioner that lies at about a 45° angle with respect to a longitudinal axis of the positioner.

8. The cochlear electrode system of claim 1 wherein the positioner further includes a pair of side walls protruding from the flexible member near a proximal end of the positioner, and wherein one side wall of the pair of side walls is adapted to lie against one side of the proximal end of the electrode array, and the other side wall of the pair of side walls is adapted to lie against an opposite side of the proximal end of the electrode array, the space between the side walls defining a proximal channel adapted to receive the proximal end of the electrode array, the proximal channel being adapted to keep the proximal end of the positioner alongside the proximal end of the electrode array when the positioner is inserted into the cochlea.

9. The cochlear electrode system of claim 8 wherein each side wall has a length, measured from a proximal edge of each side wall to a distal edge of each side wall, of from 3 to 7.5 mm.

10. The cochlear electrode system of claim 8 wherein each side wall has a maximum height, measured from a top edge of each side wall to the side of the flexible member opposite the channel, that is about 1.7 mm.

11. The cochlear electrode system of claim 8 wherein each side wall has a minimum height, measured from a top edge of each side wall to the side of the flexible member opposite the channel, that is about 0.9 mm.

12. The cochlear electrode system of claim 8 wherein each side wall has a height, measured from a top edge of each side wall to the side of the flexible member opposite the channel, that varies from a maximum height of about 1.7 mm at a proximal edge of the side wall to a height of about 0.9 mm at a distal edge of the side wall.

13. The cochlear electrode system of claim 8 wherein the proximal channel has a depth that varies from a first depth at the proximal end of the proximal channel to a second depth at a distal end of the proximal channel, the depth being measured as the distance from a floor of the proximal channel to a top edge of the side wall.

14. The cochlear electrode system of claim 13 wherein the floor of the proximal channel is raised a distance f1, with respect to the side of the flexible member opposite the proximal channel, near the proximal end of the positioner.

15. The cochlear electrode system of claim 14 wherein the amount the floor of the proximal channel is raised with respect to the side of the flexible member opposite the proximal channel varies as a function of distance from the proximal end of the positioner.

16. The cochlear electrode system of claim 15 wherein the amount the floor of the proximal channel is raised with respect to the side of the flexible member opposite the proximal channel is largest near the proximal end of the positioner and gradually decreases as the distance from the proximal end of the positioner increases.

17. The cochlear electrode system of claim 8 wherein the positioner has an opening passing longitudinally therethrough, the opening being adapted to receive a stylet wire when the positioner is being inserted into the cochlea.

18. The cochlear electrode system of claim 17 wherein the opening passing longitudinally through the positioner is closed at the distal tip of the positioner.

19. The cochlear electrode system of claim 18 further including a metal marker sealed in the closed end of the opening that passes longitudinally through the positioner, wherein the metal marker provides an identifiable reference location detectable through an imaging system.

20. The cochlear electrode system of claim 19 wherein the metal marker is made from platinum or an alloy of platinum.

21. The cochlear electrode system of claim 1 wherein the first engagement member comprises at least one engaging flap formed on the surface of the flexible carrier near the distal end of the electrode array, said at least one engaging flap having a slant associated therewith that points the flap in the general direction of the proximal end of the electrode array.

22. The cochlear electrode system of claim 21 wherein the first engagement member comprises at least five engaging flaps formed on the surface of the flexible carrier near the distal end of the electrode array, each of said engaging flaps having a slant associated therewith that points the flap in the general direction of the proximal end of the electrode array.

23. The cochlear electrode system of claim 21 wherein the second engagement member comprises a slanting frontal edge formed at the distal tip of the positioner, and wherein the slanted frontal edge is adapted to engage with the at least one engaging flap on the electrode array as the positioner is placed alongside the electrode array.

24. The cochlear electrode system of claim 23 wherein the slanted frontal edge of the positioner lies at about a 45° angle with respect to a longitudinal axis of the positioner.

25. The cochlear electrode system of claim 21 wherein the second engagement member comprises a plurality of engaging fins formed on the surface of the flexible member near the distal tip of the positioner, each of said engaging fins having a slant associated therewith that slants the fin in the general direction of the distal end of the positioner, and wherein the slanted fins are oriented so that at least one of the fins engages with the at least one engaging flap on the electrode array as the positioner is placed alongside the electrode array inside of the cochlea.

26. The cochlear electrode system of claim 25 wherein the first engagement member comprises a multiplicity of engaging flaps formed on the surface of the flexible carrier near the distal end of the electrode array, each of said engaging flaps having a slant associated therewith that points the flap in the general direction of the proximal end of the electrode array, and wherein the slanted fins of the positioner are oriented so that a plurality of the fins engage with a corresponding plurality of engaging flaps on the electrode array as the positioner is placed alongside the electrode array inside of the cochlea.

27. The cochlear electrode system of claim 1 wherein the first engagement member comprises a plurality of serrations formed on the surface of the flexible carrier near the distal end of the electrode array, each of said serrations having a slant associated therewith that points the serration in the general direction of the proximal end of the electrode array.

28. The cochlear electrode system of claim 1 wherein the first engagement member comprises a hump formed on the surface of the flexible carrier near the distal end of the electrode array, the hump being adapted to be detachably engaged with the second engagement member of the positioner as the positioner is placed alongside the electrode array inside of the cochlea.

29. The cochlear electrode system of claim 1 wherein the second engagement member comprises a plurality of serrations formed on the surface of the flexible member near the distal tip of the positioner, each of said serrations having a slant associated therewith that slants the serration in the general direction of the distal end of the positioner.

30. The cochlear electrode system of claim 1 wherein the second engagement member comprises a blade-shaped distal tip formed on the surface of the positioner, wherein the blade-shaped distal tip is adapted to engage the first engagement member of the electrode array as the positioner is inserted into the cochlea, and is further adapted to disengage the first engagement member of the electrode array when the positioner is pulled out of the cochlea.

31. A cochlear electrode system comprising:
   an electrode array, the electrode array having a first engagement member formed thereon;
   a positioner, the positioner having a second engagement member formed thereon that is detachably engageable with the first engagement member of the electrode array when the positioner is inserted into the cochlea alongside the electrode array; and
   a removable guide tube through which the positioner is inserted into the cochlea alongside the electrode array after the electrode array has been inserted into the cochlea.

32. A cochlear electrode system comprising:
   an electrode array comprising an elongate flexible carrier body having a distal end and a proximal end, a plurality of spaced-apart electrode contacts along one surface of the carrier body, and a first engagement member near the distal end of the flexible carrier body;
   a positioner, the positioner having a second engagement member formed thereon that is detachably engageable with the first engagement member of the electrode array when the positioner is inserted into the cochlea alongside the electrode array; and
   a guide tube through which the positioner is initially inserted into the cochlea alongside the electrode array once the electrode array has been inserted into the cochlea, and which guide tube is removable once the positioner has been inserted into the cochlea.

33. A cochlear electrode system comprising:
   an electrode array comprising an elongate flexible carrier body and a plurality of spaced-apart electrode contacts exposed on the carrier body, wherein the electrode array is adapted to be inserted into a human cochlea as part of a cochlear stimulation system;
   a positioner, wherein the positioner is adapted to be inserted into the cochlea alongside the electrode array and thereby better position the electrode contacts within the cochlea; and
   a guide tube through which the positioner is initially inserted into the cochlea alongside the electrode array once the electrode array has been inserted into the cochlea, and which guide tube is removable once the positioner has been inserted into the cochlea.

34. The cochlear electrode system of claim 33 wherein the electrode array has a distal end and a proximal end, and further includes first engagement means located near the proximal end for engaging with the positioner as the positioner is inserted deeper into the cochlea alongside the electrode array.

35. The cochlear electrode system of claim 34 wherein the positioner has a distal tip and a proximal end, and further includes second engagement means located at or near the distal tip for engaging with the first engagement means of the electrode array as the positioner is inserted deeper into the cochlea alongside the electrode array.

36. The cochlear electrode system of claim 35 wherein the positioner has a distal tip and a proximal end, and further includes distal keeper means near the distal tip of the positioner for keeping the distal tip of the positioner alongside the electrode array.

37. The cochlear electrode system of claim 36 wherein the positioner further includes proximal keeper means near the proximal end of the positioner for keeping the proximal end of the positioner alongside the electrode array when the positioner is inserted into the cochlea.

38. A positioner for use with an electrode array, the electrode array being adapted to be inserted into a human cochlea, the positioner comprising
   an elongate flexible member having a distal tip and a proximal end adapted to be inserted into the human cochlea alongside the electrode array, and
   an engagement member on the flexible member near the distal tip of the positioner, wherein the engagement member is detachably engageable with a distal portion of the electrode array when the positioner is inserted into the cochlea alongside the electrode array;
   wherein the positioner further has a first pair of keeper tabs protruding from the flexible member in the vicinity of the engagement member, and wherein one tab of the first pair of keeper tabs is adapted to lie against one side of the electrode array, and the other tab of the first pair of keeper tabs is adapted to lie against an opposite side of the electrode array, to thereby keep the distal end of the positioner alongside the distal portion of the electrode array when the positioner is inserted into the cochlea.

39. The positioner of claim 38 wherein the positioner has a second pair of keeper tabs protruding from the flexible member near the first pair of tabs, wherein one tab of the second pair of keeper tabs is adapted to lie against one side of the electrode array, and the other tab of the second pair of keeper tabs is adapted to lie against an opposite side of the electrode array, to thereby further keep the distal end of the positioner alongside the distal portion of the electrode array when the positioner is inserted into the cochlea.

40. The positioner of claim 39 wherein the tabs of the first and second pair of tabs are flexible, forming an integral part of the flexible member.

41. The positioner of claim 40 wherein a distal edge of the tabs of the first pair of keeper tabs is located at the distal tip.

42. The positioner of claim 41 wherein the distal tip of the positioner is formed to define a frontal edge of the positioner that lies at about a 45° angle with respect to a longitudinal axis of the positioner.

43. The positioner of claim 38 wherein the positioner further includes a pair of side walls protruding from the flexible member near the proximal end of the positioner, and wherein the space between the side walls defines a proximal channel adapted to receive the electrode array, the proximal channel being adapted to keep the proximal end of the positioner alongside the electrode array when the positioner is inserted into the cochlea.

44. The positioner of claim 43 wherein each side wall has a length measured from a proximal edge of each side wall to a distal edge of each side wall, of from 3 to 7.5 mm.

45. The positioner of claim 43 wherein each side wall has a height, measured from a top edge of each side wall to the side of the flexible member opposite the channel, that varies from a maximum height of about 1.7 mm at a proximal edge of the side wall to a height of about 0.9 mm at a distal edge of the side wall.

46. The positioner of claim 43 wherein the proximal channel has a depth that varies from a first depth at the proximal end of the proximal channel to a second depth at a distal end of the proximal channel, the depth being measured as the distance from a floor of the proximal channel to a top edge of the side wall.

47. The positioner of claim 46 wherein the floor of the proximal channel is raised a prescribed distance, with respect to the side of the flexible member opposite the proximal channel, near the proximal end of the positioner.

48. The positioner of claim 47 wherein the amount the floor of the proximal channel is raised with respect to the side of the flexible member opposite the proximal channel is largest near the proximal end of the positioner and gradually decreases as the distance from the proximal end of the positioner increases.

49. The positioner of claim wherein 38 the positioner has an opening passing longitudinally therethrough, the opening being adapted to receive a stylet wire when the positioner is being inserted into the cochlea.

50. The positioner of claim 49 wherein the opening passing longitudinally through the positioner is closed at the distal tip of the positioner.

51. The positioner of claim 50 further including a metal marker sealed in the closed end of the opening that passes longitudinally through the positioner, wherein the metal marker provides an identifiable reference location detectable through an imaging system.

52. A positioner for use with an electrode array, the electrode array being adapted to be inserted into a human cochlea, the positioner comprising an elongate flexible member having a distal tip and a proximal end adapted to be inserted into the human cochlea alongside the electrode array, and an engagement member on the flexible member near the distal tip of the positioner, wherein the engagement member is detachably engageable with a distal portion of the electrode array when the positioner is inserted into the cochlea alongside the electrode array;

an opening passing longitudinally therethrough, the opening being adapted to receive a stylet wire when the positioner is being inserted into the cochlea, wherein the opening passing longitudinally through the positioner is closed at the distal tip of the positioner;

wherein the opening that passes longitudinally through the positioner further includes a metal marker sealed in the closed end of the opening.

* * * * *